United States Patent [19]
Steinmeyer et al.

[11] Patent Number: 5,700,791
[45] Date of Patent: Dec. 23, 1997

[54] VITAMIN D DERIVATIVES MODIFIED IN THE 20-POSITION AND PHARMACEUTICAL COMPOSITIONS THEREOF

[75] Inventors: Andreas Steinmeyer; Gunter Neef; Gerald Kirsch; Katica Schwarz; Ruth Thieroff-Ekerdt; Herbert Wiesinger; Martin Haberey, all of Berlin, Germany

[73] Assignee: Schering Aktiengesellschaft, Berlin, Germany

[21] Appl. No.: 664,121

[22] Filed: Jun. 14, 1996

Related U.S. Application Data

[62] Division of Ser. No. 80,841, Jun. 24, 1993, Pat. No. 5,585,368.

[30] Foreign Application Priority Data

Jun. 24, 1992 [DE] Germany .............. 42 20 757.6

[51] Int. Cl.⁶ .................. A61K 31/59; C07C 101/00
[52] U.S. Cl. .................. 514/167; 552/653
[58] Field of Search .................. 552/653; 514/167

[56] References Cited

U.S. PATENT DOCUMENTS

| | | |
|---|---|---|
| 4,594,432 | 6/1986 | Baggiolini et al. |
| 4,612,308 | 9/1986 | Baggiolini et al. |
| 4,711,881 | 12/1987 | Ikekawa |
| 4,719,205 | 1/1988 | DeLuca et al. |
| 4,804,502 | 2/1989 | Baggiolini et al. |
| 4,832,875 | 5/1989 | Ikekawa |
| 4,851,401 | 7/1989 | DeLuca et al. |
| 4,868,165 | 9/1989 | Ikekawa |
| 4,891,364 | 1/1990 | Kubodera et al. |
| 4,970,203 | 11/1990 | DeLuca et al. |
| 5,194,431 | 3/1993 | DeLuca et al. |
| 5,200,536 | 4/1993 | Ikekawa et al. |
| 5,237,110 | 8/1993 | DeLuca et al. |
| 5,260,290 | 11/1993 | DeLuca et al. |
| 5,403,940 | 4/1995 | Vallés et al. .................. 549/300 |
| 5,446,035 | 8/1995 | Neef et al. .................. 514/167 |
| 5,583,125 | 12/1996 | Steinmeyer et al. .................. 514/167 |

FOREIGN PATENT DOCUMENTS

| | | |
|---|---|---|
| 184112 | 6/1986 | European Pat. Off. |
| 387077 | 9/1990 | European Pat. Off. |
| 521550 | 1/1993 | European Pat. Off. |
| 90/06121 | 6/1990 | WIPO |

OTHER PUBLICATIONS

Kubodera et al., "Shythetic Studies of Vidamin D . . . " *Chemical & Pharmaceutical Bulletin*, vol. 40, No. 3 (Mar. 1992) pp. 648–651.

Fernandez et al. "Synthesis of Hydrindan . . . ", *J. Org. Chem.*, vol. 57, No. 11 (May 22, 1992) pp. 3173–3178.

*Primary Examiner*—Kimberly J. Prior
*Attorney, Agent, or Firm*—Millen, White, Zelano, & Branigan, P.C.

[57] ABSTRACT

The invention relates to vitamin D derivatives, modified in 20-position, of general formula I

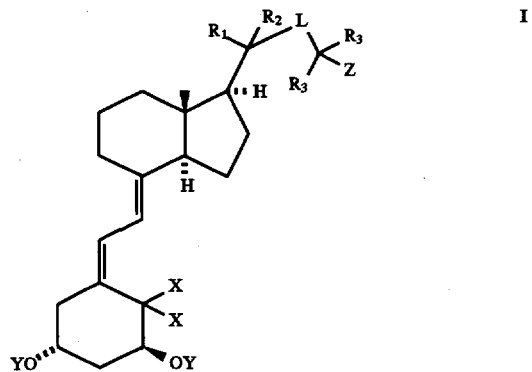

in which X, Y, Z, $R_1$, $R_2$ as well as $R_3$ have the meaning indicated in the description, process for their production and their use as agents for treatment of hyperproliferative diseases of the skin.

10 Claims, No Drawings

VITAMIN D DERIVATIVES MODIFIED IN THE 20-POSITION AND PHARMACEUTICAL COMPOSITIONS THEREOF

This is a division of the application Ser. No. 08/080,841 filed Jun. 24, 1993 now U.S. Pat. No. 5,585,368.

SUMMARY OF THE INVENTION

This invention relates to vitamin D derivatives of general formula I

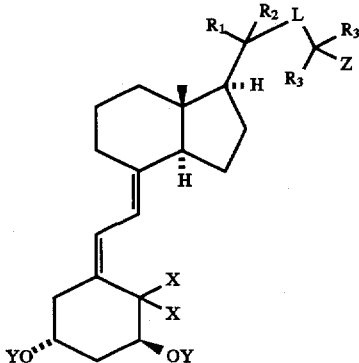

in which

Y means a hydrogen atom, an alkanoyl group with 1 to 9 carbon atoms, or an aroyl group, e.g., benzoyl, wherein each Y is chosen independently, Z means a hydrogen atom, a hydroxyl group or an alkanoyloxy group with 1 to 9 carbon atoms, X means a hydrogen atom each or both X's together mean an exocyclic methylene group, $R_1$ and $R_2$, independent of one another, mean a hydrogen atom, an alkyl group each with 1 to 4 carbon atoms, together a methylene group or together with quaternary carbon atom 20 a cyclopropyl unit, and if both X's mean a methylene group, $R_1$ and $R_2$ are not methyl, $R_3$ means a hydrogen atom each or a linear or branched alkyl group each with 1 to 5 carbon atoms, a trifluoromethyl group each or a saturated or unsaturated carbocyclic or heterocyclic 3-, 4-, 5- or 6-membered ring formed together with the tertiary carbon atom, L means grouping

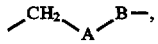

in which

A represents a methylene group, an oxygen, a sulfur, or a hydride- or $C_1$-$C_4$ alkyl-substituted nitrogen atom, and B represents an alkylene group —$(CH_2)_n$—, in which n=1, 2, 3, 4, 5 or 6 and any methylene group can be replaced by an oxygen atom, or L means grouping

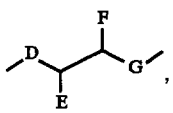

in which

D represents a direct bond, a methylene bridge or a 1,2-ethenediyl bridge (E-double bond) between carbon atoms 20 and 22, E and F respectively represent a hydrogen atom, or together a second bond (E-double bond), and G represents a direct bond or an alkylene group —$(CH_2)_n$—, in which n=1, 2, 3, 4, 5 or 6 and any methylene group can be replaced by an oxygen atom as well as each methylene group can be substituted by a hydroxyl group or a halogen atom, e.g., preferably fluorine, chlorine, or bromine, as well as a process for their production, intermediate products for this process, pharmaceutical preparations, which contain these compounds as well as their use for the production of pharmaceutical agents.

The acyl groups or acyloxy groups possible as radicals Y as well as Z are derived especially from saturated carboxylic acids or else from benzoic acid.

As alkyl groups for $R_3$, first of all, the methyl, ethyl or propyl group as well as a cyclopropyl or cyclopentyl ring formed together with the tertiary carbon atom are suitable.

Further preferred compounds according to Formula I are compounds having the following:

$R_1$ and $R_2$ each an alkyl and both X each a hydrogen;

$R_1$ and $R_2$ together a methylene group and both X each a hydrogen;

$R_1$ and $R_2$ together a methylene group and both X together a methylene group;

$R_1$ and $R_2$ together with C(20) a cyclopropyl ring and both X together a methylene group; or $R_1$ and $R_2$ together with C(20) a cyclopropyl ring and both X each a hydrogen.

Further preferred are the derivatives with the following side chains:

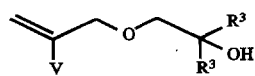 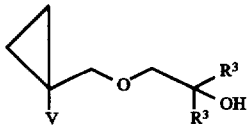 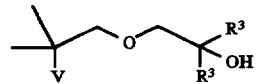

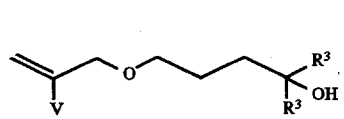 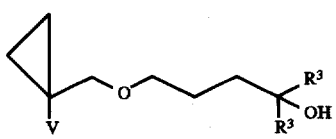 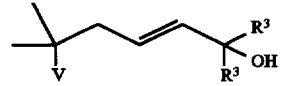

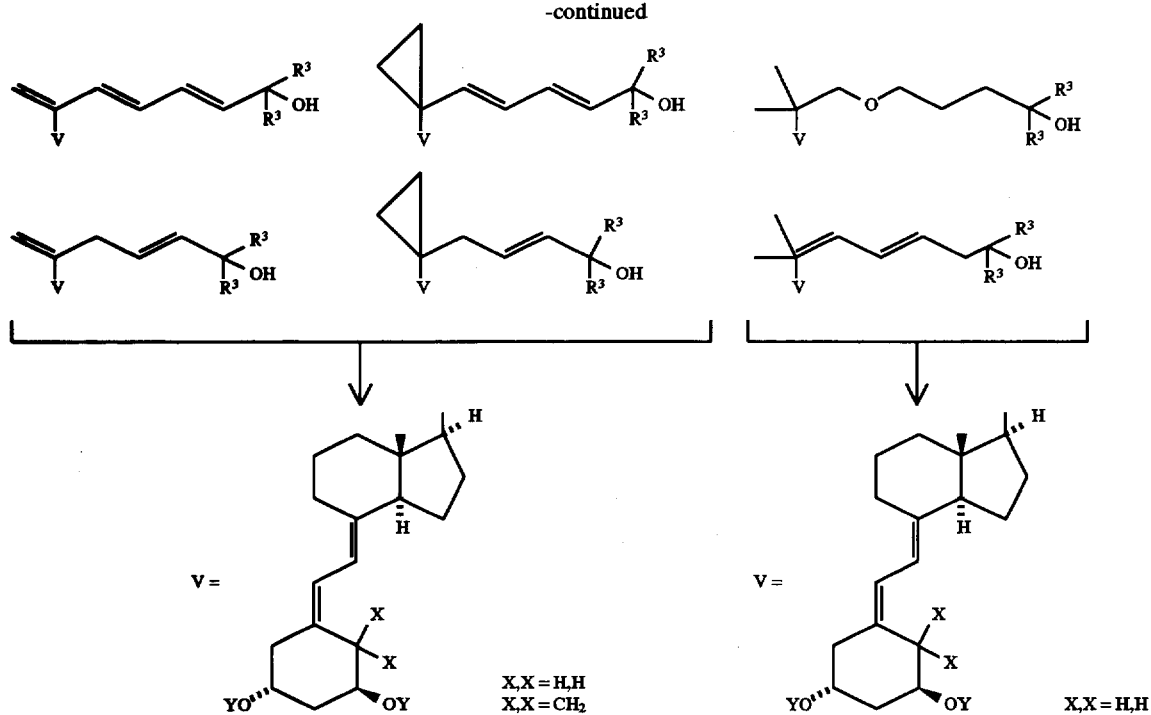

Especially preferred are the compounds:

(5Z,7E)-(1S,3R)-23-Oxa-9,10-secocholesta-5,7,10(19),20-tetraene-1,3,25-triol, (5Z,7E)-(1S,3R)-26,27-dimethyl-23-oxa-9,10-secocholesta-5,7,10(19),20-tetraene-1,3,25-triol, (5Z,7E)-(1S,3R)-26,27-diethyl-23-oxa-9,10-secocholesta-5,7,10(19),20-tetraene-1,3,25-triol, (5Z,7E)-(1S,3R)-24-(3-hydroxy-3-methylbutyl)-23-oxa-9,10-secochola-5,7,10(19),20-tetraene-1,3-diol, (5Z,7E)-(1S,3R)-24-(3-ethyl-3-hydroxypentyl)-23-oxa-9,10-secochola-5,7,10(19),20-tetraene-1,3-diol, (5Z,7E)-(1S,3R)-20,21-methylene-23-oxa-9,10-secocholesta-5,7,10(19)-tetraene-1,3,25-triol, (5Z,7E)-(1S,3R)-26,27-dimethyl-20,21-methylene-23-oxa-9,10-secocholesta-5,7,10(19)-triene-1,3,25-triol, (5Z,7E)-(1S,3R)-26,27-diethyl-20,21-methylene-23-oxa-9,10-secocholesta-5,7,10(19)-triene-1,3,25-triol, (5Z,7E)-(1S,3R)-24-(3-hydroxy-3-methylbutyl)-20,21-methylene-23-oxa-9,10-secochola-5,7,10(19)-triene-1,3-diol, (5Z,7E)-(1S,3R)-24-(3-ethyl-3-hydroxypentyl)-20,21-methylene-23-oxa-9,10-secochola-5,7,10(19)-triene-1,3-diol, (7E)-(1R,3R)-20-methyl-19-nor-23-oxa-9,10-secocholesta-5,7-diene-1,3,25-triol, (7E)-(1R,3R)-20,26,27-trimethyl-19-nor-23-oxa-9,10-secocholesta-5,7-diene-1,3,25-triol, (7E)-(1R,3R)-26,27-diethyl-20-methyl-19-nor-23-oxa-9,10-secocholesta-5,7-diene-1,3,25-triol, (7E)-(1R,3R)-24-(3-hydroxy-3-methylbutyl)-20-methyl-19-nor-23-oxa-9,10-secochola-5,7-diene-1,3-diol, (7E)-(1R,3R)-24-(3-ethyl-3-hydroxypentyl)-20-methyl-19-nor-23-oxa-9,10-secochola-5,7-diene-1,3-diol, (7E)-(1R,3R)-19-nor-23-oxa-9,10-secocholesta-5,7,20-triene-1,3,25-triol, (7E)-(1R,3R)-26,27-dimethyl-19-nor-23-oxa-9,10-secocholesta-5,7,20-triene-1,3,25-triol, (7E)-(1R,3R)-26,27-diethyl-19-nor-23-oxa-9,10-secocholesta-5,7,20-triene-1,3,25-triol, (7E)-(1R, 3R)-24-(3-hydroxy-3-methylbutyl)-19-nor-23-oxa-9,10-secochola-5,7,20-triene-1,3-diol, (7E)-(1R, 3R)-24-(3-ethyl-3-hydroxypentyl)-19-nor-23-oxa-9,10-secochola-5,7,20-triene-1,3-diol, (5Z,7E;22E)-(1S,3R)-24-(2-hydroxy-2-methylpropoxy)-9,10-secochola-5,7,10 (19),20,22-pentaene-1,3-diol, (5Z,7E,22E)-(1S,3R)-24-(2-ethyl-2-hydroxybutoxy)-9,10-secochola-5,7,10 (19), 20,22-pentaene-1,3-diol, (7E,22E)-(1R,3R)-24-(2-hydroxy-2-methylpropoxy)-19-nor-9,10-secochola-5,7,20,22-tetraene-1,3-diol, (7E,22E)-(1R,3R)-24-(2-ethyl-2-hydroxybutoxy)-19-nor-9,10-secochola-5,7,20,22-tetraene-1,3-diol.

The natural vitamins $D_2$ and $D_3$ (cf. general formula of vit. D) are biologically inactive per se and are converted to their biologically active metabolites only after hydroxylation in 25-position in the liver or in 1-position in the kidney. The action of vitamins $D_2$ and $D_3$ consists in the stabilization of the plasma-$Ca^{++}$ and plasma-phosphate level; they counteract a decline of the plasma-$Ca^{++}$ level.

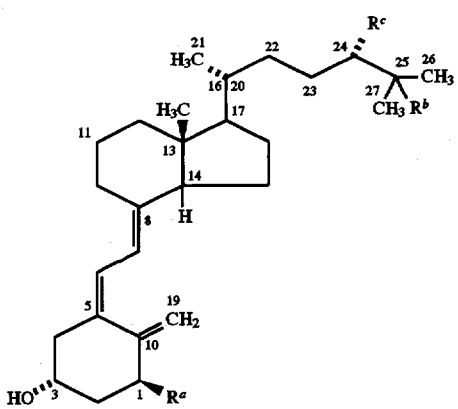

ergocalciferol: $R^a = R^b = H$, $R^c = CH_3$ vitamin $D_2$ bouble bond C-22/23
cholecalciferol: $R^a = R^b = R^c = H$ vitamin $D_3$
25-hycroxycholecalciferol: $R^a = R^c = H$, $R^b = OH$
1α-hydroxycholecalciferol: $R^a = OH$, $R^b = R^c = H$
1α-dihydroxycholecalciferol: $R^a = R^b = OH$, $R^c = H$ calcitriol In addition to their pronounced effect on the calcium and phosphate metabolism, vitamins $D_2$ and $D_3$ and their synthetic derivatives also have proliferation-inhibiting and cell-differentiating effects (H. F. De Luca, "The Metabolism and Function of Vitamin D in Biochemistry of Steroid Hormones", Editors H. L. J. Makin, 2nd Edition, *Blackwell Scientific Publications* 1984, pp. 71–116).

But with use of vitamin D, overdosage symptoms (hypercalcemia) can occur.

1α-Cholecalciferols hydroxylated in 24-position can be seen already from DE-A-25 26 981; they have a lower toxicity than the corresponding non-hydroxylated 1α-cholecalciferol. The hydroxylated compounds show a selective activation of the intestinal calcium absorption and a weaker bone absorption effect than 1α-cholecalciferol.

The 24-hydroxy vitamin D analogs described in international patent application WO 87/00834 can be used for the treatment of disorders in humans and animals caused by abnormal cell proliferation and/or cell differentiation.

For various 1,25-dihydroxy-homo-vitamin D derivatives, a dissociation relative to the properties of bone absorption effect and HL-60 cell differentiation have already been mentioned recently by De Luca. The bone absorption effect in vitro is in this case a direct measurement for the calcium immobilization in vivo.

The vitamin D activity of the compounds according to the invention is determined by the calcitriol receptor test. It is performed with use of a specific receptor protein from the intestine of young pigs (M. C. Daure, E. A. Pierce, H. F. De Luca, Proc. Natl. Acad. Sci. USA 82, 7825 (1985)).

Receptor-containing binding protein is incubated in a test tube with $^3$H-calcitriol ($5 \times 10^{-10}$ mol/l) in a reaction volume of 0.270 ml in the absence and in the presence of test substances for two hours at 4° C. To separate free and receptor-bound calcitriol, a charcoal-dextran absorption is performed. For this purpose, 250 µl of a charcoal-dextran suspension is added to each test tube and incubated at 4° C. for 20 minutes. Then, the samples are centrifuged at 10,000×g for 5 minutes at 4° C. The supernatant is decanted and measured in a β-counter after 1 hour of equilibration in Picofluor™ 15.

The competition curves obtained with various concentrations of the test substance as well as of the reference substance (unlabeled calcitriol) at a constant concentration of the reference substance ($^3$H-calcitriol) are placed in relation to one another and a competition factor (KF) is determined.

It is defined as a quotient of the concentrations of the respective test substance and the reference substance, which are necessary for 50% competition:

KF=Concentration of the test substance at 50% competition Concentration of the reference substance at 50% competition To determine the acute hypercalcemic effect of various calcitriol derivatives, the test described below is performed:

The action of control (solvent base), reference substance (1,25 $(OH)_2$-$D_3$=calcitriol) and test substance is tested respectively after one-time subcutaneous administration in groups of 10 native male rats (140–170 g). During the testing time, the rats are kept in special cages to determine the excretion of water and mineral substances. The urine is collected in 2 fractions (0–16 hours and 16–22 hours). An oral calcium load (0.1 mmol of calcium in 6.5% α-hydroxypropyl cellulose, 5 ml/animal) replaces the calcium absorption lacking by food deprivation at 1600 hours. At the end of the test, the animals are killed by decapitation and exsanguinated to determine the serum-calcium values. For the primary screen test in vivo, a single standard dose (200 µg/kg) is tested. For selected substances, the result is safeguarded by drawing up a dose-effect correlation.

A hypercalcemic effect is shown in serum-calcium level values elevated in comparison to the control.

The significance of differences between substance groups and controls as well as between test substance and reference substance is supported by suitable statistical methods. The result is indicated as dose ratio DR (DR=factor test substance dose/reference substance dose for comparable effects).

The differentiation-stimulating effect of calcitriol analogs is also detected quantitatively.

It is known in the literature (Mangelsdorf, D. J. et al., *J. Cell*. 98: 391–398 (1984)) that the treatment of human leukemia cells (promyelocyte cell line HL 60) in vitro with calcitriol induces the differentiation of cells to macrophages.

HL 60 cells are cultivated in tissue culture medium (RPMI-10% fetal calf serum) at 37° C. in an atmosphere of 5% $CO_2$ in air.

For substance testing, the cells are centrifuged off and $2.0 \times 10^5$ cells/ml in phenol red-free tissue culture medium are taken up. The test substances are dissolved in ethanol and diluted with tissue culture medium without phenol red to the desired concentration. The dilution stages are mixed with the cell suspension in a ratio of 1:10 and 100 µl each of this cell suspension mixed with substance is pipetted in an indentation of a 96-hole plate. For the control, a cell suspension is mixed analogously with the solvent.

After incubation over 96 hours at 37° C. in 5% $CO_2$ in air, 100 µl of an NBT-TPA solution (Nitro Blue Tetrazolium (NBT), end concentration in the batch of 1 mg/ml, tetradecanoyl phorbolmyristat-13-acetate (TPA), end concentration in the batch of $2 \times 10^{-7}$ mol/l) is pipetted in each indentation of the 96-hole plate in the cell suspension.

By incubation over 2 hours at 37° C. and 5% $CO_2$ in air, NBT is reduced to insoluble formazan because of the intracellular oxygen radical release, stimulated by TPA, in the cells differentiated to macrophages.

To end the reaction, the indentations of the 96-hole plate are suctioned off and the adhering cells are set by adding methanol and dried after setting. To dissolve the formed intracellular formazan crystals, 100 µl of potassium hydroxide (2 val/l) and 100 µl of dimethyl sulfoxide are pipetted in each indentation and ultrasonically irradiated for 1 minute. The concentration of formazan is spectrophotometrically measured at 650 nm.

As a measurement for the differentiation induction of the HL 60 cells to macrophages, the concentration of formed formazan applies. The result is also indicated as dose ratio (DR=factor test substance dose/reference substance dose for comparable effects).

The results of the calcitriol receptor test as well as the determination of the dose ratio of the differentiation induction of HL 60 cells and the dose ratio for hypercalcemia are summarized below: Test compounds:

(5Z,7E)-(1S,3R)-24-(3-Ethyl-3-hydroxypentyl)-23-oxa-9,10-secochola-5,7,10(19),20-tetraene-1,3-diol 16

(5Z,7E)-(1S,3R)-26,27-diethyl-20,21-methylene-23-oxa-9,10-secocholesta-5,7,10(19)-triene-1,3,25-triol 21

(7E)-(1R,3R)-20,26,27-trimethyl-19-nor-23-oxa-9,10-secocholesta-5,7-diene-1,3,25-triol 40

(7E)-(1R,3R)-24-(3-ethyl-3-hydroxypentyl)-19-nor-23-oxa-9,10-secochola-5,7,20-triene-1,3-diol 87

(5Z,7E,22E)-(1S) 3R)-24-(2-hydroxy-2-methylpropoxy)-9,10-secochola-5,7,10(19),20,22-pentaene-1,3-diol 92

(5Z,7E,22E)-(1S,3R)-24-(2-ethyl-2-hydroxybutoxy)-9,10-secochola-5,7,10(19),20,22-pentaene-1,3-diol 93

Comparison compound: calcitriol

Biological data of selected compounds:

| Compound | KF (receptor) | DR (HL 60) | DR (Calcium) |
|---|---|---|---|
| calcitriol | 1 | 1 | 1 |
| 16 | 1.6 | 0.3 | 30 |
| 21 | 2.2 | 10 | 100 |
| 40 | 1.5 | 0.2 | 5 |
| 87 | 6.3 | 1 | 100 |
| 92 | 8.3 | 1.5 | 100 |
| 93 | 2.2 | 1 | 100 |

By the reduced hypercalcemia risk, the substances according to the invention are suitable in a special way for the production of pharmaceutical agents for the treatment of diseases, which are characterized by a hyperproliferation of cells, e.g., hyperproliferative diseases of the skin (psoriasis) and malignant tumors (leukemia, colon cancer, breast cancer) and acne (J. Invest. Dermatol., Vol. 92 No. 3, 1989). The compounds according to the invention can also be used for treatment and prophylaxis of disorders, which are characterized by a disequilibrium of the immune system, for example, auto-immune diseases, including diabetes mellitus and the rejection reactions in transplantations (WO-A-91/00855). In an especially preferred embodiment of the invention, calcitriol receptors are detected before the treatment in the target organ.

Further, it has been found, surprisingly, that by topical administration of the compounds according to the invention on the skin of mice, rats and guinea pigs, an increased reddening of the skin and increase of epidermal thickness can be induced. The increase of the reddening of the skin is determined based on the increase of the red value of the skin surface quantifiable with a colorimeter. The red value is typically increased by 1.5-fold after the substance has been administered three times (dose 0.003%) at an interval of 24 hours. The increase of the epidermal thickness is quantified in the histological preparation. The number of proliferating epidermal cells (cells in the S-phase of the cell cycle) is determined flow-cytometrically and is typically increased by the factor 6.

These properties of the compounds according to the invention make them appear suitable for therapeutic use in the case of atrophic skin, as it occurs with natural skin aging, premature skin ageing because of increased exposure to light or medicinally induced skin atrophy by treatment with glucocorticoids.

Further, the healing of wounds can be accelerated by topical administration with the new compounds.

This invention thus relates also to the pharmaceutical preparations that contain at least one compound according to general formula I together with a pharmaceutically compatible vehicle.

The compounds can be formulated as solutions in pharmaceutically compatible solvents or as emulsions, suspensions or dispersions in suitable pharmaceutical solvents or vehicles or as pills, tablets or capsules, which contain solid vehicles in a way known in the art. For a topical use, the compounds are advantageously formulated as creams or ointments or in a similar form of pharmaceutical agents suitable for topical use. Each such formulation can also contain other pharmaceutically compatible and nontoxic auxiliary agents, such as, e.g., stabilizers, antioxidants, binders, dyes, emulsifiers or flavoring substances. The compounds are advantageously administered by injection or intravenous infusion of suitable sterile solutions or as oral dosage by the alimentary tract or topically in the form of creams, ointments, lotions or suitable transdermal plasters, as described in EP-A 0 387 077.

The daily dose is about 0.1 µg/patient/day—1000 µg (1 mg)/patient/day, preferably 1.0 µg/patient/day—500 µg/patient/day.

The compounds according to the invention are generally administered analogously to the administration of the known agent "calcipotriol" for treatment of psoriasis.

The invention further relates to the use of compounds according to formula I for the production of pharmaceutical agents.

The compounds of general formula I and especially the initial compounds required for their production are produced according to new processes. The invention therefore relates also to processes for the production of these compounds.

The following compounds of general formula I'

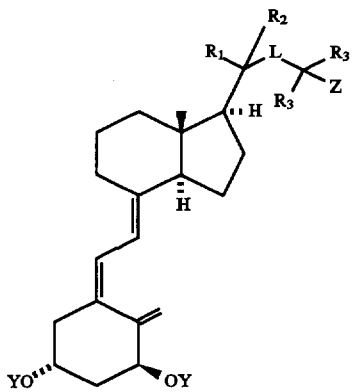

are derived from I, and the two substituents designated with X in general formula I form an exocyclic methylene group.

The starting materials for their production are the compounds of general formula VII known in the literature (see WO 90/09991, Leo Pharmaceutical Products)

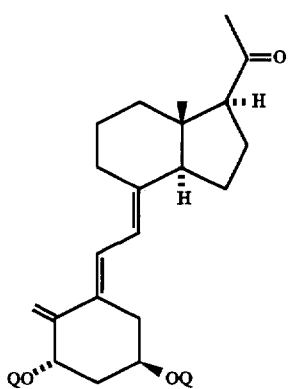

in which Q means alkyl- or aryl-substituted silyl groups.

By reaction with sulfurylidene, which is produced from reagents of the type $Me_3S^+I^-$ or $Me_3S^+(O)I^-$ by deprotonation with a base such as potassium-tert-butanolate (KOtBu), NaH or KH), compounds VIII are obtained, in which the stereo-chemistry on C-20 does not have to be uniform.

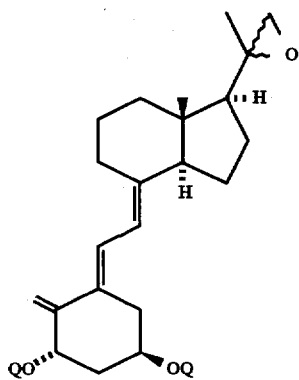

The reaction for production of VIII takes place in polar, aprotic solvents as e.g. dimethyl formamide, dimethyl sulfoxide or tetrahydrofurane (DMF, DMSO, THF).

By rearrangement of epoxides VIII with bases such as, e.g., lithium diisopropylamide (LDA), lithium diethylamide (LiNEt₂), lithium-bis(trimethylsilyl)amide (LiN(TMS)₂), aluminum isopropylate (Al(OiPr)₃), allyl alcohols IX are obtained, which can be reacted flexibly to the compounds of general formula I. See e.g., P. Welzel, H. Stein, T. Milkowa, Liebigs Ann. 2119 (1982).

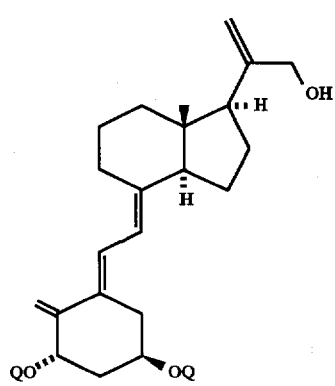

For synthesis of the compounds of general formula I', in which $R_1$ and $R_2$ together form a methylene group, L stands for grouping

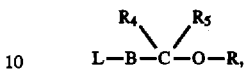         VII and A is an oxygen atom, IX is etherified with a compound of general formula X $$L—B—\overset{R_4\quad R_5}{\underset{|\quad\;\;|}{C}}—O—R, \qquad (X)$$

in which L stands for a leaving group such as Br, I, $CH_3C_6H_4SO_2O$,

B stands for an alkylene radical $—(CH_2)_n—$ with n=1, 2 or 3, and

R stands for a straight-chain or branched alkyl radical with 1 to 8 carbon atoms and $R_4$ and $R_5$ also each stand for a radical OR or $R_4$ and $R_5$ together stand for an oxygen atom, while obtaining a compound of general formula XI. See, e.g., DE 41 01 953=WO 92/12 963.

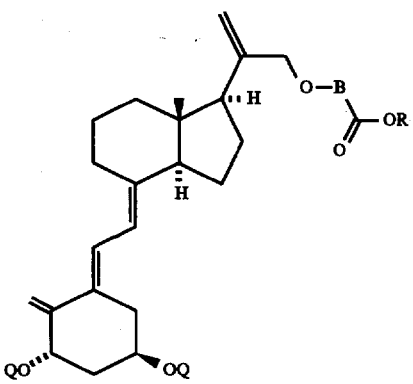

To its carbonyl group there is added a nucleophilic reagent of general formula XII, according to standard procedures.

$$R_3\text{—M} \qquad (XII)$$

in which $R_3$ means a linear or branched alkyl group with 1 to 5 carbon atoms and M means MgHal (Hal=Cl, Br, I) or an alkali atom (Li, Na, K), with formation of a compound of general formula XIII

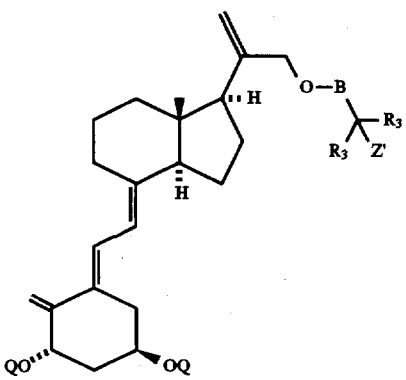

in which Z' means a hydroxyl group.

Compound XIII is converted by photochemical isomerization of the triene system in the presence of a triplet sensitizer to a compound of general formula XIV.

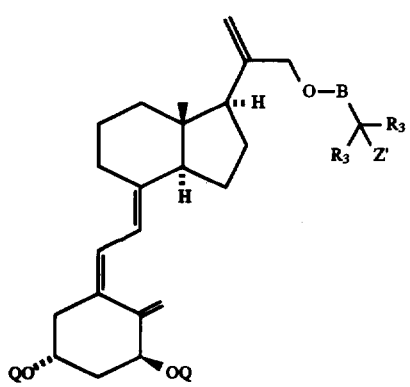

XIV

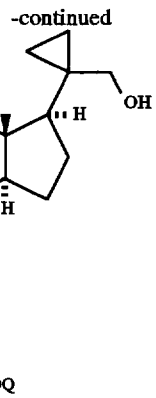

XVI

The silyl groups are cleaved off and then the free hydroxyl groups are optionally partially or completely esterified with an alkanecarboxylic acid chloride, bromide or anhydride, which in the alkanoyl radical carry 1 to 9 carbon atoms, or with benzoyl chloride.

The conversion of a compound of general formula XIII to a compound of general formula XIV takes place, e.g., by irradiation with ultraviolet light in the presence of a so-called "triplet sensitizer." Within the scope of this invention, anthracene is used for this purpose. By cleavage of the π-bond of the 5,6-double bond, rotation of the A-ring by 180° around the 5,6-single bond and reestablishing the 5,6-double bond, the stereoisomerism on the 5,6-double bond is reversed.

Then, existing hydroxy protecting groups are cleaved off, preferably with use of tetra-n-butyl-ammonium fluoride and optionally the free hydroxy groups according to conventional processes are partially or completely esterified with the corresponding carboxylic acid halide (halide=chloride, bromide) or carboxylic acid anhydride.

For synthesis of the compounds of general formula I', in which $R_1$ and $R_2$ together with quaternary carbon atom 20 form a cyclopropyl ring, and L stands for the grouping

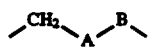

allyl alcohol IX is first isomerized photochemically to XV analogously to reaction XIII–XIV and then reacted with an organometallic reagent of type I—$CH_2$—ZN—I, which is made of Zn/Cu, Zn/Ag or $Et_2Zn$ (diethyl zinc) with $CH_2I_2$, to the compound of formula XVI (Simmons-Smith reaction, e.g., J. M. Denis, C. Girard, J. M. Conia, Synthesis 549 (1972).).

Analogously to the above-described reactions, XVI is converted by the intermediate stages of general formulas XVII and XVIII to a compound of general formula IXX, and the already described definitions and conversion possibilities apply to B, Q and Z'.

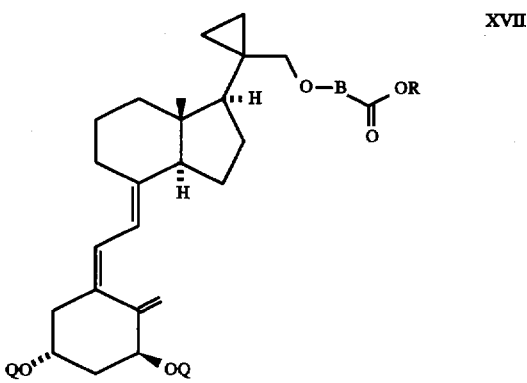

XVII

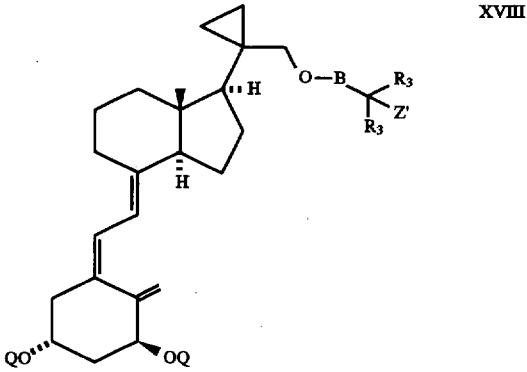

XVIII

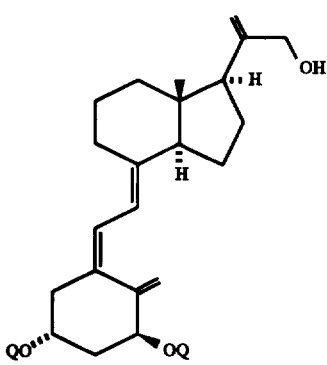

XV

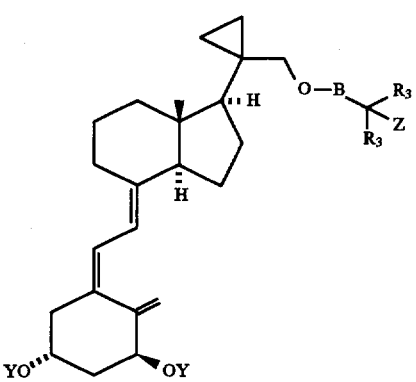

IXX

For synthesis of the compounds of general formula I'',

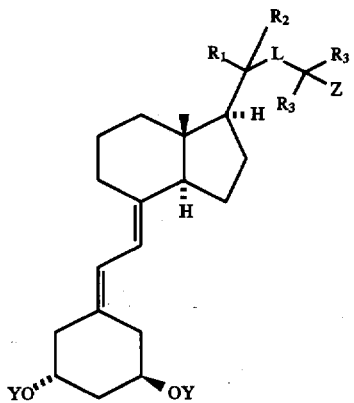

in which the two radicals X of general formula I are hydrogen atoms, and L stands for a grouping

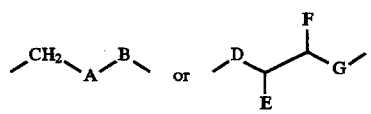

a convergent synthesis method (CD-part and A-part are made separately) is used.

As initial material, the aldehyde of general formula XX known in the literature is used (H. H. Inhoffen et al. *Chem. Ber.* 91, 780 (1958), *Chem. Ber.* 92, 1772 (1959)),

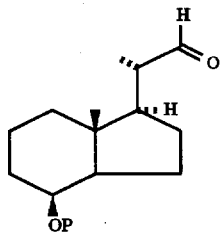

in which P means a hydrogen atom, an alkanoyl group with 1 to 9 carbon atoms, a tetrahydropyranyl or tetrahydrofuranyl group, an alkyl- or aryl-substituted or an alkyl- and aryl-substituted (mixed-substituted) silyl group. The alkanoyl group is derived preferably from straight- or branched-chain, saturated carboxylic acids; as preferred representatives, the acetyl as well as the pivaloyl groups can be mentioned as examples. As silyl groups, especially the following groups are suitable: tert-butyl-dimethylsilyl, trimethylsilyl, tert-butyl-diphenylsilyl, triphenylsilyl.

For synthesis of compounds of general formula I'', in which $R_1$ and $R_2$ each mean a methyl group, XX is deprotonated with a base such as NaH, KH, lithium diisopropylamide (LDA), potassium-tert-butanolate (KOtBu) and reacted with an electrophilic reagent $CH_3X$ (X=Cl, Br, I, $CH_3C_6H_4SO_2O$) to compound XXI, e.g., see DE 41 41 746=U.S. Ser. No. 07/988,262.

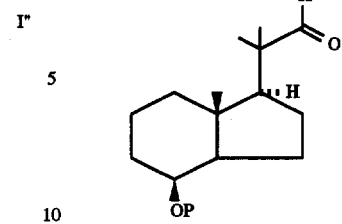

By reduction of the carbonyl group in XXI with a reducing agent such as $NaBH_4$, $NaBH_4/CeCl_3$, $LiAlH_4$ or diisobutylaluminum hydride, compound XXII is obtained,

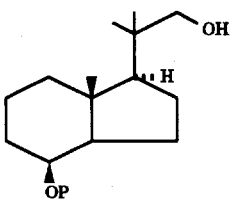

which is etherified with the already previously described compound of general formula X while obtaining a compound of general formula XXIII.

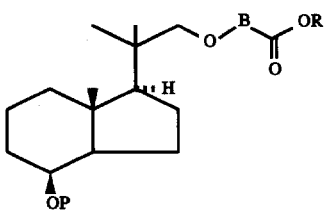

A nucleophilic reagent of general formula XII is added to the carbonyl group in XXIII, by which a compound of general formula XXIV

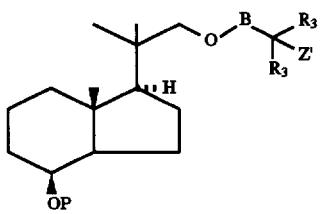

is obtained, in which Z' means a hydroxyl group.

A protecting group P optionally present in XXIV is cleaved off; in the case of an acyl group under basic conditions ($K_2CO_3$/methanol, KOH or NaOH/methanol), in the case of a silyl protecting group with fluoride reagents (tetrabutylammonium fluoride, HF, HF/pyridine) and in the case of the tetrahydropyranyl or tetrahydrofuranyl-ether protecting group under acid catalysis (p-toluenesulfonic acid, PPTS, ion exchanger) while obtaining a compound of general formula XXV

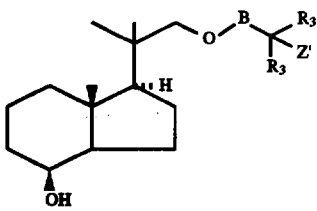   XXV whose secondary hydroxyl group is oxidized with an oxidizing agent (PCC, PDC, Collins reagent, BaMnO$_4$) and whose tertiary hydroxyl group Z' is protected, e.g., as silyl ether, preferably as trimethylsilyl ether, and a compound of general formula XXVI results,

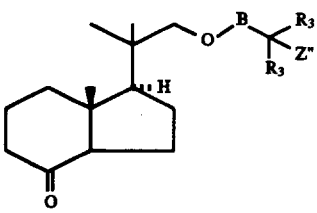   XXVI in which Z" means a silyloxy, preferably the trimethylsilyloxy group, a tetrahydropyranyl or tetrahydrofuranyl group.

By reaction with the anion of phosphine oxide XXVII known in the literature produced by a base such as n-butyllithium (BuLi) or lithium diisopropylamide (LDA) (H. F. DeLuca, Tetrahedron Lett. 32, 7663 (1991)),

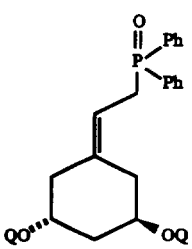   XXVII in which Q means alkyl- or aryl-substituted silyl groups, a compound of general formula XXVIII is obtained,

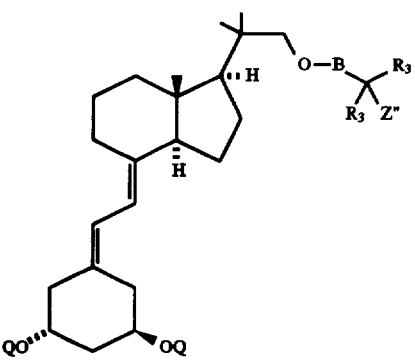   XXVIII whose protecting groups Q and Z" are cleaved as described above and the free hydroxyl groups are optionally acylated.

For the synthesis of compounds of general formula I", in which R$_1$ and R$_2$ together form a methylene group or together with quaternary carbon atom 20 form a cyclopropyl unit, aldehyde XX known in the literature is catabolized, analogously to the preparation of VII, to ketone V,

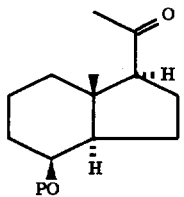   V in which P has the meaning already described.

Analogously to sequence VII-VIII-IX, V is converted by the intermediate stage of general formula XXIX to the allyl alcohol of general formula VI.

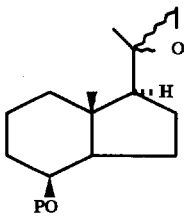   XXIX

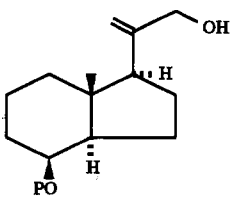   VI

In a Simmons-Smith reaction (conditions analogous to XV-XVI), the compound of general-formula XXX is obtained from VI.

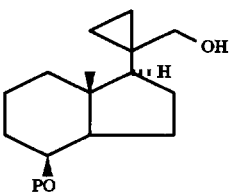   XXX

For the synthesis of compounds of general formula I", in which L stands for

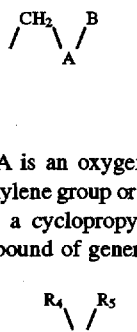

and A is an oxygen atom and R$_1$ and R$_2$ together form a methylene group or together with quaternary carbon atom 20 form a cyclopropyl unit, VI or XXV are reacted with a compound of general formula X

L—B—C—OR,   (X)

while obtaining a compound of general formula XXXI,

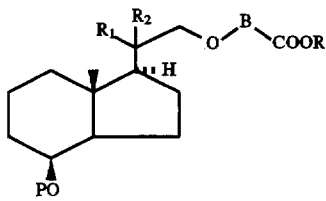

XXXI in which $R_1$ and $R_2$ as well as P have the already indicated meanings.

The conversion of a compound of general formula XXXI to a ketone of general formula XXXIV takes place as described by the intermediate products of general formulas XXXII and XXXIII.

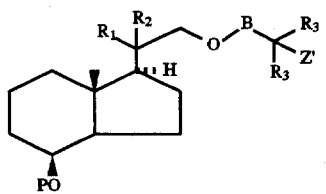

XXXII

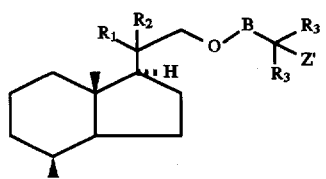

XXXIII

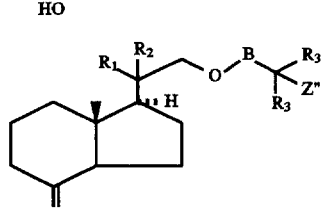

XXXIV

As described, the ketone of general formula XXXIV is now coupled with phosphine oxide XXVII known in the literature, and a compound of general formula XXXV is obtained,

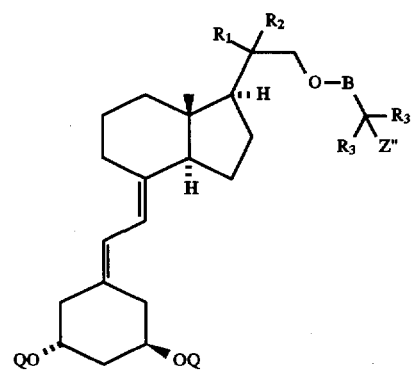

XXXV whose protecting groups are cleaved as described above and whose free hydroxy groups are optionally acylated.

For synthesis of compounds of general formula I', in which L stands for

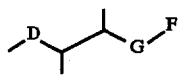

and D means a direct bond between carbon atoms 20 and 22, E and F mean an E-double bond and G means a $CH_2$—O—$CH_2$ unit, for example, an alcohol of general formula XV is oxidized with an oxidizing agent (manganese dioxide, pyridinium chlorochromate, pyridinium dichromate, barium manganate) to the aldehyde of general formula XXXVI.

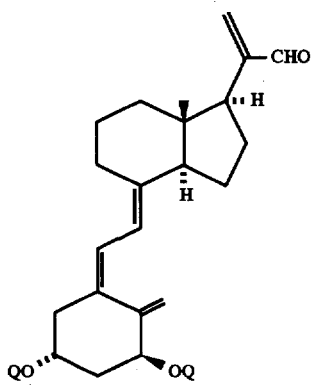

XXXVI

By Wadsworth-Emmons reaction, e.g., Wadsworth-Emmons-reaction (before Formula XXXVII): Wadsworth, Org. React 23,73 (1977) with an anion—produced by deprotonation with a base (NaH, KH, lithium diisopropylamide, potassium-tert-butanolate)—of a phosphonate of general formula XXXVII $(RO)_2P(O)$—$CH_2$—COOR'   XXXVII, in which R and R', independent of one another, mean straight-chain or branched alkyl groups with up to 9 carbon atoms or phenyl groups, a compound of general formula XXXVIII is produced,

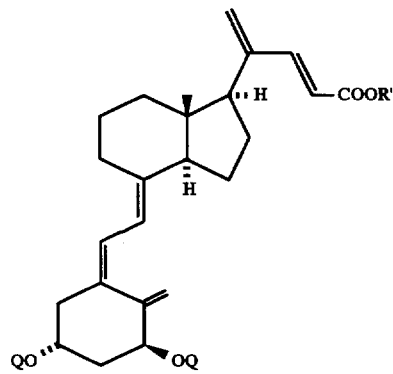

XXXVIII whose ester group is reduced with a reducing agent ($LiAlH_4$, DIBAH) in the conventional way to an alcohol of general formula XXXIX.

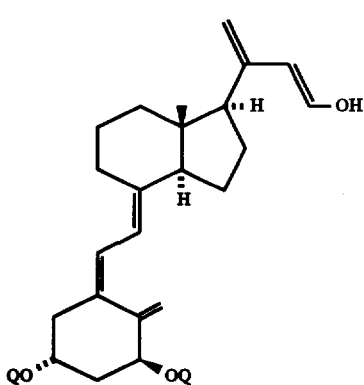

By etherification with one of the previously described compounds of general formula X, a compound of general formula XL is obtained.

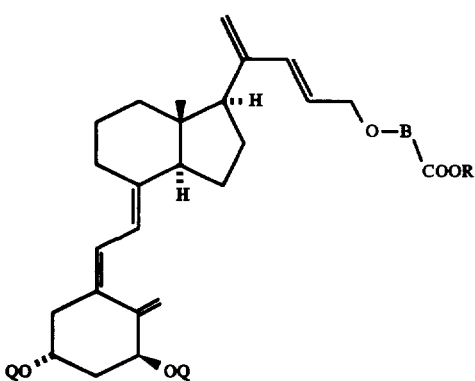

To its carbonyl group a nucleophilic reagent of already described general formula $R_3$-M (XII) is added, and a compound of general formula XLI results,

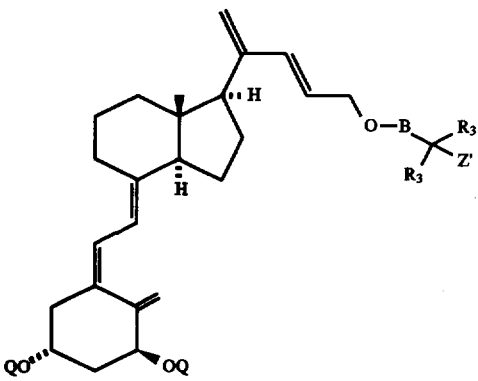

and the definitions and conversion possibilities already described for B, Q and Z' apply.

For the synthesis of the compounds of general formula I", in which L stands for

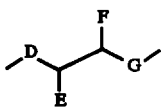

and radicals X of general formula I are hydrogen atoms and in which D, E and F as well as G have the previously described meanings, an allyl alcohol of general formula VI, analogously as described for the synthesis of the compound of general formula XLI, is oxidized to a compound of general formula XLII.

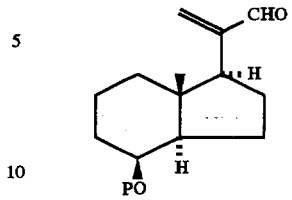

The synthesis of the side chains takes place analogously as already described for the production of the compounds of general formula XLI by the intermediate stages of general formulas XLIII, XLIV and XLV to XLVI,

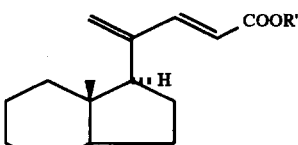

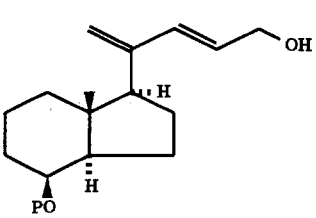

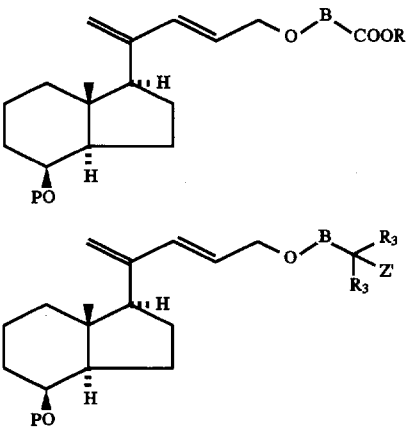

and again the already indicated definitions and conversion possibilities apply for B, Q and Z'.

By using already described methods, the synthesis of the ketone of general formula XLVIII from a compound of general formula XLVI takes place by the intermediate product of general formula XLVII.

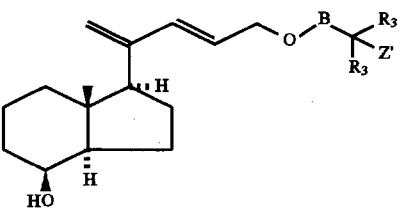

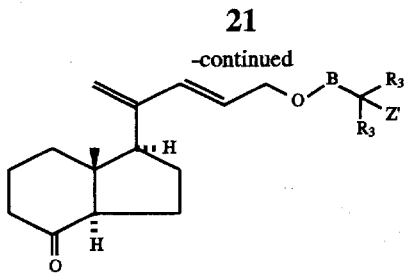XLVIII

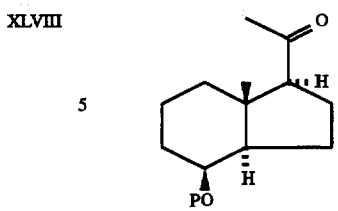V

A ketone of general formula XLVIII is coupled analogously as the compound of general formula XX with phosphine oxide XXVII known in the literature, and a compound of general formula IL is obtained,

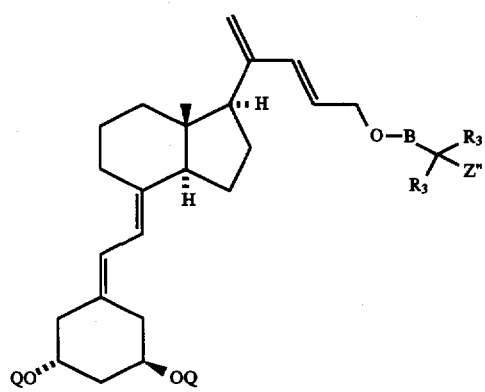IL

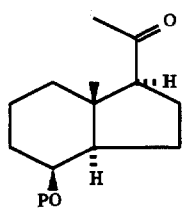VI whose protecting groups are cleaved as above and whose free hydroxyl groups are optionally acylated.

This invention also relates to the new intermediate products of general formulas IX and XV;

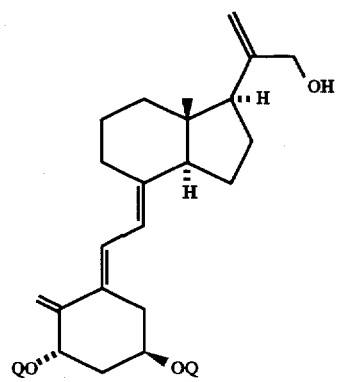IX

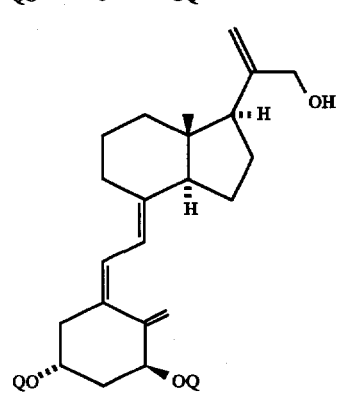XV in which Q has the already indicated meanings.

Further, the CD structural elements of general formulas V and VI as intermediate products also belong to the object of this invention:

in which P means a hydrogen atom, an alkanoyl group with 1 to 9 carbon atoms, a tetrahydropyranyl or tetrahydrofuranyl group, an alkyl- or aryl-substituted or an alkyl- and aryl-substituted (mixed-substituted) silyl group.

It especially relates to the following intermediate compounds:

(5E,7E)-(1S,3R)-1,3-bis [[1,1-Dimethylethyl) diphenylsilyl]oxy]-20-methylene-9,10-secopregna-5,7, 10(19)-trien-21-ol, (5Z,7E)-(1S,3R)-1,3-bis [[1,1-dimethylethyl) diphenylsilyl]oxy]-20-methylene-9,10-secopregna-5,7, 10(19)-trien-21-ol,

[1S-(1α,3aβ,4α,7aα)]-1-[4-(acetyloxy)-7a-methyloctahydro-1H-inden-1-yl]ethanone,

[1R-1α,3aβ,4α,7aα)]-4-[[dimethyl(1,1-dimethylethyl)-silyl]oxy]-7a-methyl-β-methylene-octahydro-1H-indene-1-ethanol.

Upon further study of the specification and appended claims, further objects and advantages of this invention will become apparent to those skilled in the art.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application German P 42 20 757.6, filed Jun. 24, 1992, are hereby incorporated by reference.

EXAMPLES 1. (5E,7E)-(1S,3R,20R)-1,3-bis[[(1,1-Dimethylethyl)-diphenylsilyl]oxy]-20,21-epoxy-20-methyl-9,10-secopregna-5,7,10(19)-triene 2

3.1 g (3.84 mmol) of (5E,7E)-(1S,3R)-bis [[(1,1-dimethylethyl) diphenylsilyl]oxy]-9,10-secopregna-5,7,10 (19)-trien-20-one 1 (bis-TBDMS-ether, see WO 90/09991, Leo Pharmaceutical Products 1 is produced analogously by use of tert.-butyldiphenylsilyl chloride instead of tert.-butyldimethylsilyl chloride) is dissolved in 70 ml of dimethylformamide under argon and mixed with 1.06 g (5.2 mmol) of trimethylsulfonium iodide. It is cooled to 0° C. and 0.51 g (5.2 mmol) of potassium-tert-butylate is added in portions. After 15 minutes at 0° C., saturated sodium chloride solution is added, it is extracted with ethyl acetate and the organic phase is washed several times with sodium chloride solution. After drying on sodium sulfate, the solvent is removed and the residue is purified on silica gel with hexane/ethyl acetate, and 2.2 g of the title compound is obtained as colorless foam.

$^1$H-NMR (CDCl$_3$): δ=0.58 ppm (s,3H,H-18), 0.89 and 0.94 (2×s; 9H,Si-t-butyl each); 1.32 (s,3H,H-21); 2.31 and 2.50 (2×d, J=5 Hz; 1H,H-22 and H-22' each); 4.19 (m, 1H,H-3); 4.59 (t,J=5.5 Hz,1H,H-1); 4.70 and 4.82 (2×s; 1H,H-19 and H-19' each); 5.57 and 6.31 (2×d,J=11 Hz; 1H,H-6 and H-7 each); 7.12–7.68 (m,20H,Si-phenyl) [The steroid numbering is used continuously].

2. (5E,7E)-(1S,3R)-1,3-bis[[(1,1-Dimethylethyl) diphenylsilyl]oxy]-20-methylene-9,10-secopregna-5,7,10(19)-trien-21-ol 3

0.28 g (3.8 mmol) of diethylamine is dissolved under argon in 35 ml of diethyl ether and 2.4 ml (3.8 mmol) of n-butyllithium solution (1.6M in hexane) is added at 0° C. After 30 minutes at this temperature, 0.72 g (0.88 mmol) of 2 is instilled in 5 ml of diethyl ether and stirred for 1 hour at 0° C. and 1 more hour at room temperature. Then, it is mixed with sodium chloride solution, extracted with ethyl acetate and the organic phase is washed with sodium chloride solution. After drying on sodium sulfate, it is concentrated by evaporation and the residue is chromatographed on silica gel with hexane/ethyl acetate, and 360 mg of the title compound is obtained as colorless foam in addition to 280 mg of the initial product.

$^1$H-NMR (CDCl$_3$): δ=0.45 ppm (s,3H,H-18); 0.99 and 1.00 (2×s; 9H,Si-t-butyl each); 4.08 and 4.17 (2×d,J=14.5 Hz; 1H,H-22 and H-22' each); 4.29 (m,1H,H-3); 4.65 (m,1H,H-1); 4.75 and 4.90 (2×s; 1H,H-19 and H-19' each); 5.03 and 5.23 (2×s; 1H,H-21 and H-21' each); 5.67 and 6.39 (2×d,J=11 Hz; 1H,H-6 and H-7 each); 7.20–7.62 (m,20H, Si-phenyl)

3. (5E,7E)-(1S,3R)-1,3-bis[[(1,1-Dimethylethyl) diphenylsilyl]oxy]-23-oxa-9,10-secochola-5,7,10(19),20-tetraene-24-carboxylic acid-1,1-dimethylethyl ester 4

800 mg (0.97 mmol) of 3 is introduced in 3 ml of toluene and 4.6 ml of aqueous sodium hydroxide solution (25%), 1.45 g (7.4 mmol) of bromoacetic acid-tert-butyl ester and 22 mg of tetrabutylammonium hydrogen sulfate are added under argon. It is stirred overnight at room temperature and then poured on sodium chloride solution. After extraction with ethyl acetate, washing the organic phase with sodium chloride solution, drying on sodium sulfate and removal of the solvent, the crude product is purified on silica gel with hexane/ethyl acetate, and 640 mg of the title compound is obtained as colorless foam.

$^1$H-NMR (CDCl$_3$): δ=0.43 ppm (s,3H,H-18); 0.96 and 0.98 (2×s; 9H,Si-t-butyl each); 1.50 (s,9H,t-butyl ester); 3.98 (s,2H,H-24); 4.02 (sbr,2H,H-22); 4.29 (m, 1H,H-3); 4.63 (m,1H,H-1); 4.72 and 4.89 (2×s; 1H,H-19 and H-19' each), 5.07 and 5.23 (2×s; 1H,H-21 and H-21' each); 5.65 and 6.39 (2×d,J=11 Hz; 1H,H-6 and H-7 each); 7.24–7.65 (m,20H,Si-phenyl)

IR (KBr): ν=1750 cm$^{-1}$ 4. (5E,7E)-(1S,3R)-1,3-bis [[(1,1-Dimethylethyl) diphenylsilyl]oxy]-23-oxa-9,10-secocholesta-5,7,10(19), 20-tetraen-25-ol 5

The Grignard reagent is prepared in 5 ml of diethyl ether from 90 mg (3.7 mmol) of magnesium chips and 522 mg (3.7 mmol) of iodomethane. At 0° C., 350 mg (0.37 mmol) of 4 is now added to 2 ml of tetrahydrofuran and stirred for 1 more hour at room temperature. It is hydrolyzed with ammonium chloride solution, the aqueous phase is extracted with ethyl acetate, the organic phase is washed with sodium chloride solution and dried on sodium sulfate. After removal of the solvent, the residue is chromatographed on silica gel with hexane/ethyl acetate and 125 mg of the title compound is obtained as colorless foam.

$^1$H-NMR (CDCl$_3$): δ32 0.43 ppm (s,3H,H-18); 0.98 (s,18H,Si-t-butyl); 1.20 (s,6H,H-26 and H-27); 3.21 (d,J=9.5 Hz,1H,H-24); 3.28 (d,J=9.5 Hz,1H,H-24'); 3.94 (d,J=12.5 Hz,1H,H-22); 4.01 (d,J=12.5 Hz,1H,H-22'); 4.30 (m, 1H,H-3); 4.53 (m,1H,H-1); 4.69 and 4.89 (2×s; 1H,H-19 and H-19' each); 5.02 and 5.20 (2×s; 1H,H-21 and H-21' each); 5.67 and 6.41 (2×d,J=11 Hz; 1H,H-6 and H-7 each); 7.25–7.65 (m,20H,Si-phenyl)

5. (5E,7E)-(1S,3R)-1,3-bis[[(1,1-Dimethylethyl) diphenylsilyl]oxy]-26,27-dimethyl-23-oxa-9,10-secocholesta-5,7,10(19),20-tetraen-25-ol 6

The Grignard reagent is prepared in 5 ml of tetrahydrofuran under argon from 350 mg (3.2 mmol) of bromoethane and 78 mg (3.2 mmol) of magnesium chips and reacted analogously to 4. with 310 mg (0.33 mmol) of 4.270 mg of the title compound is obtained as colorless foam.

$^1$H-NMR (CDCl$_3$): δ=0.46 ppm (s,3H,H-18); 0.90 (t,J=7 Hz,6H,H-28 and H-29); 0.96 and 0.98 (2×s; 9H,Si-t-butyl each); 1.56 (q,J=7 Hz,4H,H-26 and H-27); 3.27 and 3.32 (2×d,J=10 Hz,1H,H-24 and H-24' each); 3.92 and 4.01 (2×d,J=13 Hz; 1H,H-22 and H-22' each); 4.29 (m, 1H,H-3); 4.64 (m, 1H,H-1); 4.73 and 4.90 (2×s; 1H,H-19 and H-19' each); 5.03 and 5.20 (2×s; 1H,H-21 and H-21' each); 5.65 and 6.39 (2×d,J=11 Hz; 1H,H-6 and H-7 each); 7.24–7.64 (m,20H,Si-phenyl)

6. (5E,7E)-(1S,3R)-1,3-bis[[(1,1-Dimethylethyl)-diphenylsilyl]oxy]-2 6,27-diethyl-23-oxa-9,10-secocholesta-5,7,10(19),20-tetraen-25-ol 7

The Grignard reagent is prepared in 5 ml of tetrahydrofuran under argon from 390 mg (3.2 mmol) of 1-bromopropane and 78 mg (3.2 mmol) of magnesium chips and reacted analogously to 4. with 310 mg (0.33 mmol) of 4. 265 mg of the title compound is isolated as colorless foam.

$^1$H-NMR (CDCl$_3$): δ=0.44 ppm (s, 3H, H-18); 0.92 (t,J=7 Hz,6H,H-30 and H-31); 0.96 and 0.98 (2×s; 9H,Si-t-butyl each); 3.24 and 3.30 (2×d,J=11 Hz; 1H,H-24 and H-24' each); 3.91 and 4.00 (2×d,J=13 Hz; 1H,H-22 and H-22' each); 4.29 (m, 1H,H-3); 4.6.3 (m, 1H,H-1); 4.73 and 4.90 (2×s; 1H,H-19 and H-19' each); 5.02 and 5.20 (2×s; 1H,H-21 and H-21' each); 5.65 and 6.39 (2×d,J=11 Hz; 1H,H-6 and H-7 each); 7.23–7.63 (m,20H, Si-phenyl)

7. (5Z,7E)-(1S,3R)-23-oxa-9,10-secocholesta-5,7,10(19), 20-tetraene-1,3,25-triol 8

125 mg (0.14 mmol) of 5, 25 mg of anthracene and 5 μl of triethylamine in 80 ml of toluene are dissolved in a pyrex immersion reactor and irradiated for 15 minutes by a high-pressure mercury-vapor lamp (Philips HPK 125) under nitrogen atmosphere. Then, it is concentrated by evaporation, the residue is dissolved in 20 ml of tetrahydrofuran, mixed with 2.1 ml of tetrabutylammonium fluoride solution (1M in tetrahydrofuran) and stirred for 1 hour under argon at 60° C. Then, the reaction mixture is stirred in saturated sodium bicarbonate solution, extracted with ethyl acetate, dried on sodium sulfate and the solvent is removed. The product is purified by repeated chromatography on silica gel with hexane/ethyl acetate and 25 mg of the title compound is obtained as colorless foam.

$^1$H-NMR (CD$_2$Cl$_2$): δ=0.40 ppm (s,3H,H-18); 1.12 (s,6H, H-26 and H-27); 3.12 (d,J=9.5 Hz,1H,H-24); 3.18 (d,J=9.5 Hz,1H,H-24'); 3.83 (d,J=14 Hz,1H,H-22); 3.92 (d,J=14 Hz,1H,H-22'); 4.08 (m, 1H,H-3); 4.31 (m, 1H,H-1); 4.89

(s,2H,H-19 and H-21); 5.10 (s,1H,H-21'); 5.25 (s,1H,H-19'); 5.98 and 6.29 (2×d,J=11 Hz; 1H,H-6 and H-7 each)

8. (5Z,7E)-(1S,3R)-26,27-Dimethyl-23-oxa-9,10-secocholesta-5,7,10(19),20-tetraene-1,3,25-triol 9

270 mg (0.29 mmol) of 6 is reacted analogously to 7, and after the corresponding purification, 41 mg of the title compound is obtained as colorless foam.

¹H-NMR (CD₂Cl₂): δ=0.49 ppm (s,3H,H-18); 0.88 and 0.90 (2×t,J=7 Hz; 3H,H-28 and H-29 each); 1.51 (q,J=7 Hz,4H,H-26 and H-27); 3.22 and 3.30 (2×d,J=9.5 Hz; 1H,H-24 and H-24' each); 3.90 and 3.98 (2×d,J=14 Hz; 1H,H-22 and H-22' each); 4.18 (m, 1H,H-3); 4.39 (m, 1H,H-1); 4.98 (s,2H,H-19 and H-21); 5.18 (s,1H,H-21'); 5.30 (s,1H,H-19'); 6.05 and 6.38 (2×d,J=11 Hz; 1H,H-6 and H-7 each)

9. (5Z,7E)-(1S,3R)-26,27-Diethyl-23-oxa-9,10-secocholesta-5,7,10(19),20-tetraene-1,3,25-triol 10

265 mg (0.24 mmol) of 7 is reacted analogously to 7. After the corresponding purification, 38 mg of the title compound is obtained as colorless foam.

¹H-NMR (CD₂Cl₂): δ=0.48 ppm (s,3H,H-18); 0.90 (t,J=7 Hz,6H,H-30 and H-31); 3.22 and 3.28 (2×d,J=9.5 Hz,H-24 and H-24'); 3.89 and 3.98 (2×d,J=14 Hz,H-22 and H-22'); 4.18 (m, 1H,H-3); 4.39 (m, 1H,H-1); 4.98 (s,2H,H-19 and H-21); 5.17 (s,1H,H-21'); 5.30 (s,1H,H-19'); 6.04 and 6.38 (2×d,J=11 Hz; 1H,H-6 and H-7 each)

10. (5Z,7E)-(1S,3R)-1,3-bis[[(1,1-Dimethylethyl)diphenylsilyl]oxy]-20-methylene-9,10-secopregna-5,7,10(19)-trien-1-ol 11

500 mg (0.61 mmol) of 3 is dissolved in 80 ml of toluene, mixed with 80 mg (0.44 mmol) of anthracene and 15 μl of triethylamine and irradiated for 18 minutes in the apparatus described under 7. After working up and purification, 450 mg of the title compound is obtained as colorless foam.

¹H-NMR (CDCl₃): δ=0.43 ppm (s,3H,H-18); 0.95 and 1.00 (2×s; 9H,Si-t-butyl each); 4.05 and 4.15 (2×d,J=14.5Hz; 1H,H-22 and H-22' each); 4.25 (m, 1H,H-3); 4.55 (m, 1H,H-1); 4.83 (s,1H,H-19).; 5.00 (s,1H,H-21); 5.08 (s,1H,H-19'); 5.21 (s,1H,H-21'); 6.02 and 6.10 (2×d,J=11 Hz; 1H,H-6 and H-7 each); 7.15–7.68 (m,20H,Si-phenyl)

11. 3-[(5Z,7E)-(1S,3R)-1,3-bis [[(1,1-Dimethylethyl)-diphenylsilyl]oxy]-23-oxa-9,10-secochola -5,7,10(19),20-tetraen-24-yl]propanoic acid methyl ester 12

500 mg (0.61 mmol) of 11 is dissolved in 1 ml of toluene and mixed with 2.8 ml of aqueous sodium hydroxide solution (25%), 12 mg of tetrabutylammonium hydrogen sulfate and 681 mg (1.83 mmol) of 4-bromobutyric acid orthotrimethyl ester and stirred overnight at room temperature. Then, it is poured on sodium chloride solution, extracted with ethyl acetate, the organic phase is washed with sodium chloride solution, dried on sodium sulfate and the solvent is removed. After chromatographic purification, 180 mg of the title compound is obtained as colorless foam in addition to 130 mg of unreacted feedstock.

¹H-NMR (CDCl₃): δ=0.42 ppm (s,3H,H-18); 0.92 and 1.00 (2×s; 9H,Si-t-butyl each); 2.47 (t,J=7 Hz,2H,H-26); 3.70 (s,3H,COOMe); 3.46 (m,2H,H-24); 3.91 (s,2H,H-22); 4.24 (m, 1H,H-3); 4.55 (m, 1H,H-1); 4.83 (s,1H,H-19); 4.98 (s,1H,H-21); 5.08 (s,1H,H-19'); 5.17 (s,1H,H-21'); 6.03 and 6.10 (2×d,J=11 Hz; 1H,H-6 and H-7 each); 7.22–7.70 (m,20H, Si-phenyl)

12. (5Z,7E)-(1S,3R)-1,3-Bis [[(1,1-Dimethylethyl)diphenylsilyl]oxy]-24-(3-hydroxy-3-methylbutyl-23-oxa-9,10-secochola-5,7,10(19),20-tetraene 13

The Grignard reagent is prepared from 185 mg (1.3 mmol) of iodomethane and 31 mg (1.3 mmol) of magnesium chips in 5 ml of diethyl ether and reacted analogously to 4. with 120 mg (0.13 mmol) of 12, and 60 mg of the title compound is obtained as colorless foam.

¹H-NMR (CDCl₃): δ=0.42 ppm (s,3H,H-18); 0.91 and 1.00 (2×s; 9H,Si-t-butyl each); 1.23 (s,6H,H-28 and H-29); 3.48 (m,2H,H-24); 3.92 (s,2H,H-22); 4.24 (m,1H,H-3); 4.54 (m,1H,H-3); 4.83 (s,1H,H-19); 5.00 (s,1H,H-21); 5.09 (s,1H,H-19'); 5.19 (s,1H,H-21'); 6.01 and 6.09 (2×d,J=11 Hz,H-6 and H-7); 7.22–7.68 (m,20H,Si-phenyl)

13. (5Z,7E)-(1S,3R)-1,3-bis [[(1,1-Dimethylethyl) diphenylsilyl]oxy]-24-(3-ethyl-3-hydroxypentyl)-23-oxa-9,10-secochola-5,7,10(19),20-tetraene 14

The Grignard reagent is prepared in 5 ml of tetrahydrofuran from 142 mg (1.3 mmol) of bromoethane and 31 mg (1.3 mmol) of magnesium chips and reacted analogously to 4. with 120 mg (0.13 mmol) of 12. 70 mg of the title compound is obtained as colorless foam.

¹H-NMR (CDCl₃): δ32 0.42 ppm (s,3H,H-18); 0.88 (t,J=7 Hz,6H,H-30 and H-31); 0.92 and 1.00 (2×s; 9H,Si-t-butyl each); 1.49 (q,J=7 Hz,H-28 and H-29); 3.46 (m,2H,H-24); 3.91 (s,2H,H-22); 4.24 (m, 1H,H-3); 4.54 (m, 1H,H-1); 4.82 (s,1H,H-19); 4.98 (s,1H,H-21); 5.08 (s,1H,H-19'); 5.18 (s,1H,H-21'); 6.01 and 6.09 (2×d,J=11 Hz,H-6 and H-7); 7.23–7.69 (m,20H,Si-phenyl)

14. (5Z,7E)-(1S,3R)-24-(3-Hydroxy-3-methylbutyl)-23-oxa-9,10-secochola-5,7,10(19),20-tetraene-1,3-diol 15

57 mg (0.062 mmol) of 13 is dissolved in 5 ml of tetrahydrofuran, mixed with 0.67 ml of tetrabutylammonium fluoride solution (1M in tetrahydrofuran) and stirred for 1 hour at 60° C. After adding sodium chloride solution, it is extracted with ethyl acetate, the organic phase is washed with sodium chloride solution, dried on sodium sulfate and the solvent is removed. Repeated chromatography on silica gel with hexane/ethyl acetate yields 9 mg of the title compound as colorless foam.

¹H-NMR (CD₂Cl₂): δ=0.47 ppm (s,3H,H-18); 1.19 (s,6H, H-28 and H-29); 3.42 (m,2H,H-24); 3.89 (s,2H,H-22); 4.18 (m, 1H,H-3); 4.39 (m, 1H,H-1); 4.97 (s,2H,H-19 and H-21); 5.17 (s,1H,H-19'); 5.30 (s,1H,H-21'); 6.05 and 6.29 (2×d,J= 11 Hz; 1H,H-6 and H-7 each)

15. (5Z,7E)-(1S,3R)-24-(3-Ethyl-3-hydroxypentyl)-23-oxa-9,10-secochola-5,7,10 (19),20-tetraene-1,3-diol 16

67 mg (0.07 mmol) of 14 is reacted analogously to 14. with 0.76 ml of tetrabutylammonium fluoride solution in 5 ml of tetrahydrofuran and after purification, 11 mg of the title compound is obtained as colorless foam.

¹H-NMR (CD₂Cl₂): δ=0.47 ppm (s,3H,H-18); 0.84 (t,J=7 Hz,6H,H-30 and H-31); 1.47 (q,J=7 Hz,H-28 and H-29); 3.40 (m,2H,H-24); 3.89 (m,2H,H-22); 4.18 (m, 1H,H-3); 4.39 (m,1H,H-1); 4.97 (s,2H,H-19 and H-21); 5.16 (s,1H, H-19'); 5.30 (s,1H,H-21'); 6.04 and 6.38 (2×d,j=11 Hz,H-6 and H-7)

16. (5Z,7E)-(1S,3R)-1,3-bis[[(1,1-Dimethylethyl) diphenylsilyl]oxy]-20,21-methylene-9,10-secopregna-5,7, 10(19),20-triene-20-methanol 17

The zinc/silver reagent is prepared from zinc powder and silver acetate analogously to J. M. Conia et al. (*Synthesis* 549 (1972)). 98 mg (1.5 mmol) of the reagent is now introduced in 5 ml of diethyl ether under argon and 268 mg (1 mmol) of diiodomethane is instilled slowly, and a slight boiling of the reaction solution starts. It is stirred for 30 minutes: at room temperature and then 200 mg (0.24 mmol) of 11 in 5 ml of diethyl ether is added. It is stirred for 1 hour at room temperature and then 0.2 ml of pyridine is added. The resulting precipitate is filtered off and the filtrate is diluted with ethyl acetate, the organic phase is washed with sodium bicarbonate and sodium chloride solution, dried on sodium sulfate and the solvent is removed. The residue is purified by chromatography on silica gel with hexane/ethyl acetate, and 65 mg of the title compound is obtained as colorless foam.

$^1$H-NMR (CDCl$_3$): δ=0.20 ppm (m,1H,cyclopropyl); 0.34 (m,2H, cyclopropyl); 0.55 (s,3H,H-18); 0.66 (m,1H, cyclopropyl); 0.92 and 0.99 (2×s; 9H,Si-t-butyl each); 3.04 and 3.92 (2×dbr, J=10.5 Hz; 1H,H-22 and H-22' each); 4.23 (m,1H,H-3); 4.54 (m,1H,H-1); 4.82 and 5.09 (2×s; 1H,H-19 and H-19' each); 5.98 and 6.10 (2×d,J=11 Hz; 1H,H-6 and H-7 each); 7.22–7.68 (m,20H,Si-phenyl)

17. (5Z,7E)-(1S,3R)-1,3-bis [[(1,1-Dimethylethyl)diphenylsilyl]oxy]-2 0,2 1-methylene-23-oxa-9,10-secochola-5,7,10(19)-triene-24-carboxylic acid-1,1-dimethylethyl ester 18

130 mg of 17 in 1 ml of toluene is reacted with 0.16 g (0.81 mmol) of bromoacetic acid-tert-butyl ester, 0.7 ml of aqueous sodium hydroxide solution and 3 mg of tetrabutylammonium hydrogen sulfate analogously to 3. After working up, 80 mg of the title compound is obtained as colorless foam.

1H-NMR (CD$_2$Cl$_2$): δ=0.28–0.42 ppm (m, $^3$H,cyclopropyl); 0.53 (s,3H,H-18); 0.62 (m,1H, cyclopropyl); 0.90 and 0.98 (2×s; 9H,Si-t-butyl each); 1.50 (s,9H,t-butyl ester); 2.99 (dbr,J=10.5 Hz,1H,H-22); 3.72 (d,J=10 Hz,1H,H-24); 3.90 (dbr, J=10.5 Hz,1H,H-22'); 3.90 (d,J=10 Hz,1H,H-24'); 4.25 (m, 1H,H-3); 4.55 (m, 1H,H-1); 4.82 and 5.08 (2×s; 1H,H-19 and H-19' each); 5.99 and 6.12 (2×d,J=11 Hz; 1H,H-6 and H-7 each); 7.28–7.68 (m,20H, Si-phenyl)

18. (5Z,7E)-(1S,3R)-20,21-Methylene-23oxa-9,10-secocholesta-5,7,10(19)-triene-1,3,25-triol 19

The Grignard reagent is prepared in 5 ml of diethyl ether from 170 mg (1.2 mmol) of iodomethane and 30 mg (1.2 mmol) of magnesium chips and analogously to 4., reached with 120 mg (0.13 mmol) of 18. The crude product obtained here is reacted directly with 1.1 ml of tetrabutylammonium fluoride solution in tetrahydrofuran analogously to 14., and after chromatographic purification, 14 mg of the title compound is obtained as colorless foam.

$^1$H-NMR (CD$_2$Cl$_2$): δ=0.14–0.30 ppm (m, 3H,cyclopropyl); 0.54 (s,3H,H-18); 1.02 (m,1H, cyclopropyl); 1.18 (s,6H,H-26 and H-27); 2.82 (d,J=10 Hz,1H,H-22); 3.05 (d,J=9.5 Hz,1H,H- 24); 3.17 (d,J=9.5 Hz,1H,H-24'); 3.68 (d,J=10 Hz,1H,H-22'); 4.09 (m,1H,H-3); 4.30 (m,1H,H-1); 4.88 and 5.21 (2×s; 1H,H-19 and H-19' each); 5.91 and 6.28 (2×d,J=11Hz; 1H,H-6 and H-7 each)

19. (5Z,7E)-(1B,3R)-26,27-Dimethyl-20,21-methylene-23-oxa-9,10-secocholesta-5,7,10(19)-triene-1,3,25-triol 20

The Grignard reagent, which is reacted with 80 mg (0.1 mmol) of 18 analogously to 4., is prepared from 19.4 mg (0.8 mmol) of magnesium chips and 88 mg (0.8 mmol) of bromoethane. The crude product is then dissolved in 5 ml of tetrahydrofuran and reacted with 0.85 ml of tetrabutylammonium fluoride solution in tetrahydrofuran analogously to 14. After repeated chromatography on silica gel with hexane/ethyl acetate, 22 mg of the title compound is obtained as colorless foam.

$^1$H-NMR (CD$_2$Cl$_2$): δ=0.21–0.40 ppm (m, 3H,cyclopropyl); 0.52 (s,3H,H-18); 0.85 (t,J=7 Hz,6H,H-28 and H-29); 0.89 (m,1H,cyclopropyl); 1.49 (q,J=7 Hz,4H,H-26 and H-27); 2.88 (dbr,J=10.5 Hz,1H,H-22); 3.17 (d,J=10 Hz,1H,H-24); 3.26 (d,J=10 Hz,1H,H-24'); 3.72 (dbr,J=10.5 Hz,1H,H-22'); 4.17 (m,1H,H-3); 4.39 (m,1H,H-1); 4.97 and 5.29 (2×s; 1H,H-19 and H-19' each); 6.00 and 6.38 (2×d,J=11 Hz; 1H,H-6 and H-7 each)

20. (5Z,7E)-(1S,3R)-26,27-Diethyl-20,21-methylene-23-oxa-9,10-secocholesta-5,7,10(19)-triene-1,3,25-triol 21

The Grignard reagent is prepared from 163 mg (1.3 mmol) of 1-bromopropane and 32 mg (1.3 mmol) of magnesium chips in 5 ml of tetrahydrofuran and reacted analogously to 4. with 125 mg (0.13 mmol) of 18. The crude product is treated analogously to 14. with 0.72 ml of tetrabutylammonium fluoride solution in 5 ml of tetrahydrofuran and after repeated chromatography, 26 mg of the title compound is obtained as colorless foam.

$^1$H-NMR (CD$_2$Cl$_2$): δ=0.20–0.37 ppm (m, 3H,cyclopropyl); 0.90 (t,J=7 Hz,6H,H-30 and H-31); 1.08 (m,1H,cyclopropyl); 2.87 (d,J=10 Hz,1H,H-22); 3.13 (d,J=9.5 Hz,1H,H-24); 3.23 (d,J=9.5 Hz,1H,H-24'); 3.70 (d,J=10 Hz,1H,H-22'); 4.17 (m,1H,H-3); 4.37 (m, 1H,H-1); 4.93 and 5.28 (2×s; 1H,H-19 and H-19' each); 5.98 and 6.35 (2×d,J=11 Hz; 1H, H-6 and H-7 each)

21. 3-[(5Z,7E)-(1S,3R)-1,3-bis[[(1,1-Dimethylethyl)diphenylsilyl]oxy]-20,21-methylene-23-oxa-9,10-secochola-5,7,10(19)-trien-24-yl]propanoic acid methyl ester 22

400 mg (0.48 mmol) of 17, 2.2 ml of aqueous sodium hydroxide solution (25%), 10 mg of tetrabutylammonium hydrogen sulfate and 536 mg (1.44 mmol) of 4-bromobutyric acid orthotrimethyl ester are reacted in 1 ml of toluene analogously to 11. Purification yields 100 mg of the title compound as colorless foam in addition to 310 mg of initial material.

$^1$H-NMR (CDCl$_3$): δ=0.18–0.35 ppm (m, 3H,cyclopropyl); 0.47 (s,3H,H-18); 0.53 (m,1H, cyclopropyl); 0.88 and 0.97 (2×s; 9H,Si-t-butyl each); 2.37 (t,J=7 Hz,2H,H-26); 2.74 (d,J=10.5 Hz,1H,H-22); 3.35 (m,2H,H-24); 3.60 (s,3H,COOMe); 3.62 (d,J=10.5 Hz,1H, H-22'); 4.17 (m, 1H,H-3); 4.48 (m,1H,H-1); 4.76 and 5.02 (2×s; 1H,H-19 and H-19' each); 5.90 and 6.02 (2×d,J=11 Hz; 1H,H-6 and H-7 each); 7.20–7.60 (m,20H,Si-phenyl)

22. (5Z,7E)-(1S,3R)-1,3-bis [[(1,1-Dimethylethyl)diphenylsilyl]oxy]-24-(3-ethyl-3-hydroxypentyl)-20,21-methylene-23-oxa-9,10-secochola-5,7,10 (19)-triene 23

The Grignard reagent is prepared from 305 mg (2.8 mmol) of bromoethane and 68 mg (2.8 mmol) of magnesium chips in 5 ml of tetrahydrofuran and reacted analogously to 4. with 145 mg (0.15 mmol) of 22. 103 mg of the title compound is obtained as colorless foam.

$^1$H-NMR (CDCl$_3$): δ32 0.28–0.45 ppm (m,3H, cyclopropyl); 0.52 (s,3H,H-18); 0.61 (m, 1H,cyclopropyl); 0.88 (t,J=7 Hz,6H,H-30 and H-31); 0.90 and 0.99 (2×s; 0.9H,Si-t-butyl each); 2.86 (d,J=10 Hz,1H,H-22); 3.39 (m,2H,H-24); 3.70 (d,J=10 Hz,1H,H-22'); 4.23 (m,1H,H-3); 4.54 (t,J=6 Hz,1H,H-1); 4.82 and 5.09 (2×s; 1H,H-19 and H-19' each); 5.98 and 6.09 (2×d,J=11 Hz; 1H,H-6 and H-7 each); 7.22–7.68 (m,20H,Si-phenyl)

23. (5Z,7E)-(1S,3R)-24-(3-Ethyl-3-hydroxypentyl)-20,21-methylene-23-oxa-9,10-secochola-5,7,10(19)-triene-1,3-diol 24

100 mg (0.1 mmol) of 23 in 5 ml of tetrahydrofuran is reacted with 1 ml of tetrabutylammonium fluoride analogously to 11. and after purification, 21 mg of the title compound is obtained as colorless foam.

$^1$H-NMR (CD$_2$Cl$_2$): δ32 0.10–0.29 ppm (m, 3H,cyclopropyl); 0.51 (s,3H,H-18); 0.78 (t,J=7 Hz,H-30 and H-31); 1.01 (m,1H,cyclopropyl); 1.38 (q,J=7 Hz,4H,H-28 and H-29); 2.78 (d,J=10 Hz,1H,H-22); 3.28 (m,2H,H-24); 3.58 (d,J=10 Hz,1H,H-22'); 4.09 (m,1H,H-3); 4.30 (m,1H, H-1); 4.88 and 5.22 (2×s; 1H,H-19 each); 5.91 and 6.29 (2×d,J=11 Hz; 1H,H-6 and H-7 each) 24. [1S-(1α,3αβ,4α,7aα)]-4-(Acetyloxy)octahydro-α,α,7a-trimethyl-1H-indene-1-acetaldehyde 25

A suspension of 900 mg (30 mmol) of sodium hydride (80%) in 120 ml of tetrahydrofuran is prepared and a solution of 6.3 g (25 mmol) of [1R-[1α(S*),3aβ,4α,7aα]]-4-(acetyloxy)-α,7a-dimethyloctahydro-1H-indene-1-acetaldehyde (H. H. Inhoffen et al. Chem. Ber. 91, 780 (1958), Chem. Ber. 92, 1772 (1959)) is instilled in 60 ml of tetrahydrofuran at 0° C. under argon. After 30 minutes, 19.65 g (75 mmol) of methyl iodide is instilled and then it is stirred for 6 hours at 50° C. After the cooling, the reaction mixture is poured on sodium chloride solution, extracted with ethyl acetate, the organic phase is washed with sodium chloride solution, dried on sodium sulfate and the solvent is removed. The residue is chromatographed on silica gel with hexane/ethyl acetate, and 3.2 g of the title compound is obtained as colorless oil.

$^1$H-NMR (CDCl$_3$): δ=0.82 ppm (s,3H,H-18); 1.05 and 1.08 (2×s; 3H,H-21 and C-20-methyl each); 1.99 (s,3H,OAc); 5.09 (m, 1H,H-8); 9.60 (s,1H,H-22)

IR (film): ν=1725, 1710 cm$^{-1}$

25. [1S-(1α,3aβ,4α,7aα)]-4-(Acetyloxy)octahydro-β,β,7a-trimethyl-1H-indene-1-ethanol 26

350 mg (1.3 mmol) of 25 is dissolved in 5 ml of tetrahydrofuran and 5 ml of methanol and 193 mg (1.4 mmol) of cerium trichloride-heptahydrate is added. 46 mg (1.2 mmol) of sodium borohydride is now added in portions at 0° C. and it is stirred for 1 more hour. Then, it is hydrolyzed with sodium chloride solution, extracted with ethyl acetate, the organic phase is washed with sodium chloride solution, dried on sodium sulfate and concentrated by evaporation. The residue is purified on silica gel with hexane/ethyl acetate, and 285 mg of the title compound remains as colorless oil.

$^1$H-NMR (CDCl$_3$): δ=0.90 ppm (s,3H,H-18); 1.00 and 1.01 (2×s; 3H,H-21 and C-20-methyl each); 2.05 (s,3H,OAc); 3.29 and 3.37 (2×d,J=10.5 Hz; 1H,H-22 and H-22' each); 5.16 (m, 1H,H-8)

IR (film): ν=1725 cm$^{-1}$

26. [1S-(1α,3aβ,4α,7aα)]-1,1-Dimethylethyl-[2-[4-(acetyloxy)-7a-methyloctahydro-1H-inden-1-yl]-2-methylpropoxy]acetate 27

3.04 g (11.3 mmol) of 26 is dissolved in 40 ml of toluene, 11.9 g (61.3 mmol) of bromoacetic acid-tert-butyl ester, 33.9 ml of aqueous sodium hydroxide solution (25%) and 172 mg of tetrabutylammonium hydrogen sulfate are added under argon. It is now stirred for 48 hours at room temperature and then poured on sodium chloride solution. After extraction with ethyl acetate, washing of the organic phase with sodium chloride solution, drying on sodium sulfate and removal of the solvent, the residue is chromatographed on silica gel with hexane/ethyl acetate, and 1.1 g of the title compound is obtained as colorless oil in addition to 1.93 g of initial material.

$^1$H-NMR (CDCl$_3$): δ=0.88 ppm (s,3H,H-18); 0.93 and 0.99 (2×s; 3H,H-21 and C-20-methyl each); 1.41 (s,9H,t-butyl ester); 1.99 (s,3H,OAc); 3.03 and 3.20 (2×d, J=9 Hz; 1H,H-22 and H-22' each); 3.82 and 3.90 (2×d, J=16 Hz; 1H,H-24 and H-24' each); 5.09 (m, 1H,H-8)

27. [1S-(1α,3aβ,4α,7aα)]-1-[1,1-Dimethyl-2-(2-ethyl-2-hydroxybutoxy) ethyl]-7a-methyloctahydro-1H-inden-4-ol 28

The Grignard reagent is prepared in 20 ml of tetrahydrofuran from 10.8 g (100 mmol) of bromoethane and 928 mg (88 mmol) of magnesium chips and 1.1 g (2.8 mmol) of 27 in 39 ml of tetrahydrofuran is added at 0° C. It is stirred for 1 more hour at room temperature and the reaction mixture then is poured on saturated ammonium chloride solution. After extraction with ethyl acetate, washing the organic phase with sodium chloride solution, drying on sodium sulfate and evaporating the solvent, the crude product is purified by chromatography on silica gel with hexane/ethyl acetate, and 995 mg of the title compound is obtained as colorless oil.

$^1$H-NMR (CDCl$_3$): δ=0.88 ppm (s,3H,H-18); 0.90 (t,J=7 Hz,6H,H-28 and H-29); 1.00 and 1.07 (2×s; 3H,H-21 and C-20-methyl each); 1.51 (q,J=7 Hz,4H,H-26 and H-27); 3.11 and 3.16 (2×d, J=9.5 Hz; 1H,H-22 and H-22' each); 3.21 and 3.27 (2×d, J=9.5 Hz; 1H,H-24 and H-24' each); 4.09 (m, 1H,H-8)

28. [1S-(1α,3aβ,4α,7aα)]-1-[1,1-Dimethyl-2-(2-hydroxy-2-methylpropoxy)ethyl]-7a-methyloctahydro-1H-inden-4-ol 29

The Grignard reagent is prepared from 2.04 g (14.4 mmol) of iodomethane and 350 mg (14.4 mmol) of magnesium chips in 20 ml of diethyl ether and reacted analogously to 27. with 690 mg (1.8 mmol) of 27. 410 mg of the title compound is obtained as colorless oil.

$^1$H-NMR (CDCl$_3$): δ=0.87 ppm (s,1H,H-18); 0.94 and 1.00 (2×s; 3H,H-21 and C-20-methyl each); 1.15 (s,3H,H-26 and H-27); 2.31 (sbr,1H,OH); 3.09 (s,2H,H-22); 3.11 (d,J=9.5 Hz,1H,H-24); 3.18 (d,J=9.5 Hz,1H,H-24'); 4.02 (m, 1H,H-8)

29. [1S-(1α,3aβ,4α,7aα)]-1-[1,1-Dimethyl-2-(2-hydroxy-2-propylpentoxy)ethyl]-7a -methyloctahydro-1H -inden -4-ol 30

The Grignard reagent is prepared from 1.97 g (14.4 mmol) of 1-bromopropane and 350 mg (14.4 mmol) of magnesium chips in 20 ml of tetrahydrofuran and reacted analogously to 27. with 690 mg (1.8 mmol) of 27. 630 mg of the title compound is obtained as colorless oil.

$^1$H-NMR (CDCl$_3$): δ=0.82 ppm (s,3H,H-18); 0.84 (t,J=7 Hz,6H,H-30 and H-31); 0.93 and 0.98 (2×s; $^3$H,H-21 and C-20-methyl each); 2.29 (t,J=6 Hz,1H,OH); 3.07 (s,2H,H-22); 3.12 (d,J=9.5 Hz,1H,H-24); 3.18 (d,J=9.5 Hz,1H,H-24'); 4.01 (m,1H,H-8)

30. [1S-(1α,3aβ,7aα)]-1-[1,1-Dimethyl-2-(2-ethyl-2-hydroxybutoxy)ethyl]-7a-methyloctahydro-4H-inden-4-one 31

890 mg (2.8 mmol) of 28 in 10 ml of methylene chloride under argon is instilled in a suspension of 1.41 g (6.6 mmol) of pyridinium chlorochromate in 50 ml of methylene chloride. After 2 hours at room temperature, it is diluted with diethyl ether, filtered several times on Celite and the solvent is removed. The residue is chromatographed on silica gel with hexane/ethyl acetate, and 696 mg of the title compound is obtained as colorless oil.

$^1$H-NMR (CDCl$_3$): δ=0.72 ppm (s,3H,H-18); 0.90 (t,J=7 Hz,6H,H-28 and H-29); 0.92 and 1.02 (2×s; 3H,H-21 and C-20-methyl each); 1.52 (q,J=7 Hz,4H,H-26 and H-27); 3.18 (s,2H,H-22); 3.22 and 3.28 (2×d,J=9.5 Hz; 1H,H-24 and H-24' each)

31. [1S-(1α,3aβ,7aα)]-1-[1,1-Dimethyl-2-(2-hydroxy-2-methylpropoxy)ethyl]-7a -methyloctahydro-4H -inden-4-one 32

410 mg (1.37 mmol) of 29 in 20 ml of methylene chloride is reacted with 379 mg (1.76 mmol) of pyridinium chlorochromate analogously to 30. and 273 mg of the title compound is obtained as colorless oil.

$^1$H-NMR (CDCl$_3$): δ32 0.76 ppm (s,3H,H-18); 0.88 and 0.97 (2×s; 1H,H-21 and C-20-methyl each); 1.15 (s,6H,H-26 and H-27); 2.36 (dd,J=10.5,7.5 Hz,1H,H-14); 3.12 (s,2H,H-22); 3.12 (d,J=9.5 Hz,1H,H-24); 3.19 (d,J=9.5 Hz,1H,H-24')

32. [1S-(1α,3aβ,7aα)]-1-[1,1-Dimethyl-2-(2-hydroxy-2-propylpentoxy)ethyl]-7a-methyloctahydro-4H-inden-4-one 33

640 mg (1.83 mmol) of 30 in 20 ml of methylene chloride is reacted with 503 mg (2.34 mmol) of pyridinium chlorochromate analogously to 30., and 386 mg of the title compound is obtained as colorless oil.

¹H-NMR (CDCl₃): δ=0.75 ppm (s,3H,H-18); 0.86 (t,J=7 Hz,6H, H-30 and H-31); 0.86 and 0.95 (2×s; 3H,H-21 and C-20-methyl each); 2.35 (dd, J=10.5,7.5 Hz,1H,H-14); 3.08 (s,2H,H-22); 3.13 (d,J=9.5,2H,H-22); 3.18 (d,J=9.5 Hz,1H, H-22')

33. [1S-(1α,3aβ,7aα)]-1-[1, 1-Dimethyl-2-[2-ethyl-2-[ (trimethylsilyl)oxy]butoxy]ethyl]-7a-methyloctahydro-4H-inden-4-one 34

696 mg (2.1 mmol) of 31, 571 mg (8.4 mmol) of imidazole and 456 mg (4.2 mmol) of trimethylchlorosilane are dissolved in 10 ml of dimethylformamide and stirred overnight at room temperature under argon. Then, it is mixed with sodium chloride solution, extracted with ethyl acetate, the organic phase is washed with sodium chloride solution, dried on sodium sulfate and the solvent is removed. The residue is chromatographed on silica gel with hexane/ethyl acetate, and 766 mg of the title compound remains as colorless oil.

¹H-NMR (CD₂Cl₂): δ=0.10 ppm (s,9H, SiMe₃); 0.70 (s,3H,H-18); 0.82 (t,J=7 Hz,6H,H-28 and H-29); 0.91 and 1.03 (2×s; 3H,H-21 and C-20-methyl each); 1.53 (q,J=7 Hz,4H, H-26 and H-27); 3.05 and 3.13 (2×d,J=9 Hz; 1H,H-22 and H-22' each); 3.20 and 3.24 (2×d,J=9.5 Hz; 1H,H-24 and H-24' each)

34. [1S-(1α,3aβ,7aα)]-1-[1,1-Dimethyl-2-[2-methyl-2-[ (trimethylsilyl)oxy]propoxy]ethyl]-7a-methyloctahydro-4H-inden-4-one 35

270 mg (0.92 mmol) of 32 is reacted with 300 mg (2.76 mmol) of trimethylchlorosilane, 248 mg (3.59 mmol) of imidazole and 0.37 ml of pyridine in 30 ml of diethyl ether analogously to 33., and 272 mg of the title compound is obtained as colorless oil. ¹H-NMR (CDCl₃): δ=0.11 ppm (s,9H,SiMe₃); 0.72 (s,3H,H-18); 0.91 and 1.02 (2×s; 3H,H-21 and C-20-methyl each); 1.23 (s,6H,H-26 and H-27); 2.41 (dd,J=10.5,7.5 Hz,1H,H-14); 3.11 (d,J=9.5 Hz,1H,H-22); 3.14 (2×d,J=9.5 Hz; 1H,H-22' and H-24 each); 3.19 (d,J=9.5 Hz, 1H, H-24')

35. [1S-(1α,3aβ,7aα)]-1-[1,1-Dimethyl-2-[2-propyl-2-[ (trimethylsilyl)oxy]pentoxy]ethyl]-7a-methyloctahydro-4H-inden-4-one 36

383 mg (1.10 mmol) of 33 is reacted with 358 mg (3.30 mmol) of trimethylchlorosilane, 296 mg (4.29 mmol) of imidazole and 0.44 ml of pyridine in 30 ml of diethyl ether analogously to 33., and 386 mg of the title compound is obtained as colorless oil.

¹H-NMR (CDCl₃): δ=0.11 ppm (s,9H, SiMe₃); 0.73 (s,3H,H-18); 0.90 (t,J=7 Hz,6H,H-30 and H-31); 0.91 and 1.03 (2×s; 3H,H-21 and C-20-methyl each); 2.42 (dd,J=10.5, 7.5 Hz,1H,H-14); 2.92 and 3.00 (2×d,J=9.5 Hz; 1H,H-22 and H-22' each); 3.08 and 3.12 (2×d,J=9.5 Hz; 1H,H-24 and H-24' each)

36. (7E)-(1R, 3R)-1,3-bis [[(Dimethyl(1,1-dimethylethyl) silyl]oxy]-20,26,27-trimethyl-25-[(trimethylsilyl)oxy]-19-nor-23-oxa-9,10-secocholesta-5,7-diene 37

200 mg (0.35 mmol) of (3R-trans)-[2-[3,5-bis [[di-methyl (1,1-dimethylethyl)silyl]oxy]-cyclohexylidene]-ethyl] diphenylphosphine oxide (H. F. De Luca et al. Tetrahedron Lett. 32, 7663 (1991)) is dissolved in 10 ml of tetrahydrofuran and cooled under argon to −70° C. 0.21 ml (0.36 mmol) of n-butyllithium solution (1.6M in hexane) is instilled. After 5 minutes, 277 mg (0.7 mmol) of 34 in 4 ml of tetrahydrofuran is instilled and stirred for 30 minutes at this temperature. Then, it is hydrolyzed with potassium-sodium tartrate/potassium bicarbonate solution, extracted with ethyl acetate, the organic phase is washed with sodium chloride solution, dried on sodium sulfate and the solvent is removed. The residue is chromatographed on silica gel with hexane/ethyl acetate, and 80 mg of the title compound is obtained as colorless foam.

¹H-NMR (CDCl₃): δ=0.00 ppm (s,12H,SiMe₂); 0.07 (s,9H,SiMe₃); 0.58 (s,3H,H-18); 0.80 (t,J=7 Hz,6H,H-28 and H-29); 0.82 (s,18H,Si-t-butyl); 0.88 and 0.98 (2×s; 3H,H-21 and C-20-methyl each); 2.98 and 3.08 (2×d,J=9 Hz; 1H, H-22 and H-22' each); 3.12 and 3.18 (2×d,J=9.5 Hz; 1H,H-24 and H-24' each); 4.02 (m,2H,H-1 and H-3); 5.76 and 6.12 (2×d,J=11 Hz; 1H,H-6 and H-7 each)

37. (7E)-(1R,3R)-1,3-bis[[(Dimethyl(1,1-dimethylethyl) silyl]oxy]-20-methyl-25-[(trimethylsilyl)oxy]-19-nor-23-oxa-9,10-secocholesta-5,7-diene 38

61 mg (0.16 mmol) of 33 is reacted analogously to 36. and 75 mg of the title compound is obtained as colorless foam.

¹H-NMR (CD₂Cl₂): δ=0.04, 0.05, 0.11 ppm (3×s,21H, SiMe); 0.62 (s,3H,H-18); 0.87 and 0.88 (2×s; 9H,Si-t-butyl each); 0.90 and 1.01 (2×s; 3H,H-21 and C-20-methyl each); 1.22 (s,6H,H-26 and H-27); 3.10 (d,J=9.5 Hz,H-22); 3.12 (d,J=9.5 Hz,1H,H-24); 3.17 (d,J=9.5 Hz,1H,H-22'); 3.18 (d,J=9.5 Hz,1H,H-24'); 4.08 (m,2H,H-1 and H-3); 5.80 and 6.18 (2×d,J=11 Hz; 1H,H-6 and H-7 each)

38. (7E)-(1R,3R)-1,3-bis[[Dimethyl(1,1-dimethylethyl) silyl]oxy]-26,27-diethyl-20-methyl-25-[(trimethylsilyl)oxy] -19-nor-23-oxa-9,10-secocholesta-5,7-diene 39

126 mg (0.30 mmol) of 35 is reacted analogously to 36. and 193 mg of the title compound is reacted as colorless foam.

¹H-NMR (CD₂Cl₂): δ=0.04, 0.05, 0.10 ppm (3×s,21H, SiMe); 0.62 (s,3H,H-18); 0.88 (t,J=7 Hz,6H,H-30 and H-31); 0.87 (2×s; 9H,Si-t-butyl each); 0.92 and 1.02 (2×s; 3H,H-21 and C-20-methyl each); 3.03 and 3.12 (2×d,J=9.5 Hz; 1H,H-22 each); 3.18 and 3.21 (2×d,J=9.5 Hz; 1H,H-24 each); 4.08 (m,2H,H-1 and H-3); 5.81 and 6.18 (2×d,J=11 Hz; 1H,H-6 and H-7 each)

39. (7E)-(1R,3R)-20,26,27-Trimethyl-19-nor-23-oxa-9,10-secocholesta-5,7-diene-1,3,25-triol 40

80 mg (0.106 mmol) of 37 is dissolved in 12 ml of tetrahydrofuran, 183 mg (0.58 mmol) of tetrabutylammonium fluoride is added under argon and stirred for 2 hours at 55° C. Then, it is mixed with sodium chloride solution, extracted with ethyl acetate, the organic phase is washed with sodium chloride solution, dried on sodium sulfate and the solvent is removed. The residue is chromatographed on silica gel with hexane/ethyl acetate, and 24 mg of the title compound is obtained as colorless crystals.

¹H-NMR (CD₂Cl₂): δ=0.63 ppm (s,3H,H-18); 0.85 (t,J=7 Hz,6H,H-28 and H-29); 0.93 and 1.00 (2×s; 3H,H-21 and C-20-methyl each); 1.49 (q,J=7 Hz,4H,H-26 and H-27); 3.15 and 3.17 (2×d,J=9 Hz; 1H,H-22 and H-22' each); 3.22 and 3.27 (2×d,J=9.5 Hz; 1H,H-24 and H-24' each); 3.98 and 4.07 (2×m; 1H,H-1 and H-3 each); 5.85 and 6.28 (d,J=11 Hz; 1H,H-6 and H-7 each)

UV (MeOH): λ_max=251 nm, mp: 155° C.

40. (7E)-(1R,3R)-20-Methyl-19-nor-23-oxa-9,10-secocholesta-5,7-diene -1,3,25-trio 41

72 mg (0.10 mmol) of 38 in 5 ml of tetrahydrofuran is reacted with 234 mg (0.75 mmol) of tetrabutylammonium fluoride analogously to 39. and after purification, 29 mg of the title compound is obtained as colorless foam.

¹H-NMR (CD₂C₁₂): δ=0.57 ppm (s,3H,H-18); 0.87 and 0.94 (2×s; 3H,H-21 and C-20-methyl each); 1.10 (s,6H,H-26 and H-27); 3.09 (d,J=9.5 Hz,1H,H-24); 3.10 (s,2H,H-22); 3.13 (d,J=9.5 Hz,1H,H-24'); 3.91 and 3.99 (2×m; 1H,H-1 and H-3 each); 5.77 and 6.20 (d,J=11 Hz; 1H,H-6 and H-7 each)

41. (7E)-(1R,3R)-26,27-Diethyl-20-methyl-19-nor-23-oxa-9,10-secocholesta-5,7-diene-1,3,25-triol 42

190 mg (0.24 mmol) of 39 in 12 ml of tetrahydrofuran is reacted with 571 mg (1.83 mmol) of tetrabutylammonium fluoride analogously to 39. and, after purification, 87 mg of the title compound is obtained as colorless foam.

$^1$H-NMR (CD$_2$C1$_2$): δ=0.57 ppm (s,3H,H-18); 0.84 (t,J=7 Hz,6H,H-30 and H-31); 0.85 and 0.92 (2×s; 3H,H-21 and C-20-methyl each); 3.08 (s,2H,H-22); 3.11 (d,J=9.5 Hz,1H, H-24); 3.17 (d,J=9.5 Hz,1H,H-24'); 3.91 and 3.99 (2×m; 1H,H-1 and H-3 each); 5.77 and 6.20 (2×d,J=11 Hz;1H,H-6 and H-7 each)

42. [1S-(1α,3aβ,4α,7aα)]-4-[[Dimethyl(1,1-dimethylethyl)silyl]oxy]octahydro-α,α,7a-trimethyl-1H-indene-acetaldehyde 43

9.2 g (28.34 mmol) of [1R-[1α(S*),3aβ,4α,7aα]]-α,7a-dimethyl-4-[[dimethyl-(1,1-dimethylethyl)silyl]oxy]-octahydro-1H-indene-1-acetaldehyde (W. G. Dauben et al. Tetrahedron Lett. 30, 677 (1989) is reacted with 1.02 g (34.05 mmol) of sodium hydride (80%) and 12.07 g (85.03 mmol) of iodomethane in 130 ml of tetrahydrofuran analogously to 24., and 7.89 g of the title compound is obtained as colorless oil.

$^1$H-NMR (CDCl$_3$): δ=0.01 ppm (2×s; 3H,SiMe each); 0.88 (s,9H, Si-t-butyl); 0.98 (s,3H,H-18); 1.09 and 1.12 (2×s; 3H,H-21 and C-20-methyl each); 4.01 (m,1H,H-8); 9.68 (s,1H,H-22)

43. [1S-(1α,3aβ,4α,7aα)]-4-[[Dimethyl(1,1-dimethyl-ethyl)silyl]oxy]octahydro-α,α,7a-trimethyl-1H-indene-1-ethanol 44

3.5 g (10.33 mmol) of 43 is reacted with 1.53 g (11.1 mmol) of cerium trichloride heptahydrate and 365 mg (9.53 mmol) of sodium borohydride in 27 ml of tetrahydrofuran/27 ml of methanol analogously to 25. 2.36 g of the title compound is obtained as colorless oil.

$^1$H-NMR (CDCl$_3$): δ=0.01 ppm (2×s; 3H,SiMe each); 0.89 (s,9H,Si-t-butyl); 0.89 (s,3H,H-18); 0.99 and 1.05 (2×s; 3H,H-21 and H-20-methyl each); 1.60 (t,J=5 Hz,1H,OH); 3.30 (dd,J=11, 5.5 Hz,1H,H-22); 3.36 (dd, J=11.5 Hz,1H, H-22'); 4.00 (m,1H,H-8)

44. [1S-(1α,3aβ,4α,7aα)]-4-[2-[4-[[Dimethyl(1,1-dimethyl-ethyl)silyl]oxy]-7a-methyl-octahydro-1H-inden-1-yl]-2-methylpropoxy]butanoic acid methyl ester 45

2.36 g (6.93 mmol) of 44 is reacted with 6.3 g (27.7 mmol) of 4-bromobutyric acid orthotrimethyl ester and 366 mg of tetrabutylammonium hydrogen sulfate in 9.3 ml of sodium hydroxide solution (25%) and 3 ml of toluene analogously to 11., and 3.14 g of the title compound is obtained as colorless oil.

$^1$H-NMR (CDCl$_3$): δ32 0.01 ppm (2×s; 3H,SiMe each); 0.89 (s,9H,Si-t-butyl); 0.89 (s,3H,H-18); 0.98 and 1.03 (2×s; 3H,H-21 and C-20-methyl each); 2.41 (t,J=7 Hz,2H,H-26); 3.03 (d,J=9 Hz,1H,H-22); 3.10 (d,J=9 Hz,1H,H-22'); 3.38 (t,J=7 Hz,2H,H-24); 3.70 (s,3H, COOMe); 4.00 (m,1H,H-8)

45. [1S-(1α,3aβ,4α,7aα)]-5-[2-[4-[[Dimethyl(1,1-dimethethyl)silyl]oxy]-7a-methyl-octahydro-1H-inden-1-yl]-2-methylpropoxy]-2-methyl-2-pentanol 46

The Grignard reagent is prepared from 1.21 g (8.5 mmol) of iodomethane and 206 mg (8.5 mmol) of magnesium chips in 10 ml of diethyl ether and reacted with 750 mg (1.7 mmol) of 45 analogously to 27. 453 mg of the title compound is obtained as colorless oil.

$^1$H-NMR (CDCl$_3$): δ=0.02 ppm (2×s; 3H,SiMe each); 0.89 (s,9H,Si-t-butyl); 0.92 (s,3H,H-18); 1.00 and 1.04 (2×s; 3H,H-21 and C-20-Me each); 1.22 (s,6H,H-28 and H-29); 3.09 (d,J=9.5 Hz,1H,H-22); 3.18 (d,J=9.5 Hz,1H,H-22'); 3.42 (t,J=7 Hz,2H,H-24); 4.00 (m,1H,H-8)

46. [1S-(1α,3aβ,4α,7aα)]-1-[2-[4-[[Dimethyl(1,1-dimethylethyl)silyl]oxy]-7a-methyl-octahydro-1H-inden-1-yl]-2-methylpropoxy]-4-ethyl-4-hexanol 47

The Grignard reagent is prepared from 935 mg (8.5 mmol) of bromoethane and 206 mg (8.5 mmol) of magnesium chips in 20 ml of tetrahydrofuran and reacted analogously to 27. with 750 mg (1.7 mmol) of 45. 412 mg of the title compound is obtained as colorless oil.

$^1$H-NMR (CDCl$_3$): δ=0.01 ppm (2×s; 3H,SiMe each); 0.88 (t,J=7 Hz,6H,H-30 and H-31); 0.89 (s,9H,Si-t-butyl); 0.90 (s,3H,H-18); 1.00 and 1.04 (2×s; 3H,H-21 and C-20-methyl each); 1.48 (q,J=7 Hz,4H,H-28 and H-29); 3.07 (d,J=9.5 Hz,1H,H-22); 3.14 (d,J=9.5 Hz,1H,H-22'); 3.40 (t,J=7 Hz,2H,H-24); 3.99 (m, 1H,H-8)

47. [1S-(1α,3aβ,4α,7aα)]-1-[1,1-Dimethyl-[2-(4-hydroxy-4-methylpentoxy)ethyl]-7a-methyloctahydro-1H-inden-4-ol 48

400 mg (0.91 mmol) of 46 in 8.2 ml of tetrahydrofuran/acetonitrile (1:1) is stirred with 4.1 ml of hydrofluoric acid (40%) for 30 minutes at room temperature. It is neutralized with diluted sodium hydroxide solution, extracted with ethyl acetate, the organic phase is washed with sodium chloride solution and dried on sodium sulfate. After removal of the solvent the residue is chromatographically purified, and 266 mg of the title compound is obtained as colorless oil.

$^1$H-NMR (CDCl$_3$): δ=0.84 ppm (s,3H,H-18); 0.92 and 1.00 (2×s; 3H,H-21 and C-20-methyl each); 1.17 (s,6H,H-28 and H-29); 3.01 and 3.09 (2×d,J=9.5 Hz; 1H, H-22 and H-22' each); 3.36 (t,J=7 Hz,2H,H-24); 4.00 (m, 1H,H-8)

48. [1S-(1α,3aβ,4α,7aα)]-1-[1,1-Dimethyl-[2-(4-ethyl-4-hydroxyhexoxy)ethyl]-7a-methyloctahydro-1H -inden-4-ol 49

412 mg (0.87 mmol) of 47 is reacted with 3.9 ml of hydrofluoric acid (40%) in 7.8 ml of tetrahydrofuran/acetonitrile (1:1) analogously to 47., and 251 mg of the title compound is obtained as colorless oil.

$^1$H-NMR (CDCl$_3$): δ=0.80 ppm (t,J=7 Hz,6H,H-30 and H-31); 0.82 (s,3H,H-18); 0.93 and 0.99 (2×s; 3H,H-21 and C-20-methyl each); 1.42 (q,J=7 Hz,4H,H-28 and H-29); 3.00 and 3.08 (2×d,J=9.5 Hz; 1H,H-22 and H-22' each); 3.33 (t,J=7 Hz,2H,H-24); 4.00 (m, 1H,H-8)

49. [1S-(1α,3aβ,7aα)]-1-[1,1-Dimethyl-[2-(4-hydroxy-4-methylpentoxy)ethyl]-7a-methyloctahydro-4H-inden-4-one 50

260 mg (0.80 mmol) of 48 is reacted with 240 mg (1.12 mmol) of pyridinium chlorochromate in 16 ml of methylene chloride analogously to 30., and 201 mg of the title compound is obtained as colorless oil.

$^1$H-NMR (CDCl$_3$): δ32 0.69 ppm (s,3H,H-18); 0.88 and 1.01 (2×s; 3H,H-21 and C-20-methyl each); 1.22 (s,6H,H-28 and H-29); 2.42 (dd,J=10.5,7.5 Hz,1H,H-14); 3.07 and 3.13 (2×d,J=9.5 Hz; 1H,H-22 and H-22' each); 3.39 (t, J=7 Hz, 2H,H-24)

50. [1S-(1α,3αβ,7aα)]-1-[1, 1-Dimethyl-[2-(4-ethyl-4-hydroxyhexoxy) ethyl]-7a-methyloctahydro -4H-inden-4-one 51

251 mg (0.71 mmol) of 49 is reacted with 212 mg (0.99 mmol) of pyridinium chlorochromate in 16 ml of methylene chloride analogously to 30., and 183 mg of the title compound is obtained as colorless oil.

$^1$H-NMR (CDCl$_3$): δ=0.70 ppm (s,3H,H-18); 0.86 (t,J=7 Hz,6H,H-30 and H-31); 0.90 and 1.01 (2×s; 3H,H-21 and H-20-methyl each); 1.48 (q,J=7 Hz,4H,H-28 and H-29); 2.42 (dd,J=10.5,7.5 Hz,1H,H-14); 3.08 and 3.15 (2×d,J=9.5 Hz; 1H,H-22 and H-22' each); 3.40 (t,J=7 Hz,2H,H-24)

51. [1S-(1α,3aβ,7aα)]-1-[1,1-Dimethyl-[2-[4-methyl-4-[(trimethylsilyl)oxy]pentoxy]ethyl]-7a-methyloctahydro-4H-inden-4-one 52

201 mg (0.62 mmol) of 50 is reacted with 205 mg (1.86 mmol) of trimethylchlorosilane, 167 mg (2.42 mmol) of imidazole and 0.25 ml of pyridine in 15 ml of diethyl ether analogously to 33., and 194 mg of the title compound is obtained as colorless oil.

$^1$H-NMR (CDCl$_3$): δ=0.11 ppm (s,9H,SiMe$_3$); 0.82 (s,3H, H-18); 0.90 and 1.01 (2×s; 3H,H-21 and C-20-methyl each); 1.22 (s,6H,H-29 and H-30); 2.43 (dd,J=10.5,7.5 Hz,1H,H-14); 3.07 and 3.12 (2×d,J=9.5 Hz; 1H,H-22 each); 3.37 (z,J=7 Hz,2H,H-24)

52. [1S-(1α,3aβ,7a α)]-1-[1,1-Dimethyl-[2-[4-ethyl-4-[(trimethylsilyl)oxy]hexoxy]ethyl]-7a-methyloctahydro-4H-inden-4-one 53

183 mg (0.52 mmol) of 51 is reacted with 171 mg (1.56 mmol) of trimethylchlorosilane, 140 mg (2.03 mmol) of imidazole and 0.21 ml of pyridine in 15 ml of diethyl ether analogously to 33., and 178 mg of the title compound is obtained as colorless oil.

$^1$H-NMR (CDCl$_3$): δ=0.10 ppm (s, 9H, SiMe$_3$); 0.70 (s,3H,H-18); 0.82 (t,J=7 Hz,6H,H-30 and H-31); 0.91 and 1.00 (2×s; 3H,H-21 and C-20-methyl each); 2.42 (dd, J=10.5,7.5 Hz,1H,H-14); 3.05 and 3.11 (2×d,J=9.5 Hz; 1H,H-22 each); 3.35 (t,J=7 Hz,2H,H-24)

53. (7E)-(1R, 3R)-1,3-bis[[Dimethyl(1,1-dimethylethyl)silyl]oxy]-20-methyl-24-[3-methyl-3-[(trimethylsilyl)oxy]butyl]-19-nor-23-oxa-9,10-secochola-5,7-diene 54

100 mg (0.25 mmol) of 52 is reacted analogously to 36., and 130 mg of the title compound is obtained as colorless foam.

$^1$H-NMR (CDCl$_3$): δ=0.01 and 0.08 ppm (2×s, 21H, SiMe$_3$ and SiMe); 0.58 (s,3H,H-18); 0.82 (s,18H, Si-t-butyl); 0.86 and 0.97 (2×s; 3H, H-21 and C-20-methyl each); 1.18 (s,6H,H-28 and H-29); 3.01 and 3.09 (2×d,J=9.5 Hz; 1H,H-22 and H-22' each); 3.32 (t,J=7 Hz,2H,H-24); 4.03 (m,2H,H-1 and H-3); 5.76 and 6.12 (2×d,J=11 Hz; 1H,H-6 and H-7 each)

54. (7E)-(1R, 3R)-1,3-bis[[Dimethyl(1,1-dimethylethyl)silyl]oxy]-20-methyl-24-[3-ethyl-3-[(trimethylsilyl)oxy]pentyl]-19-nor-23-oxa-9,10-secochola-5,7-diene 55

100 mg (0.24 mmol) of 53 is reacted analogously to 36., and 111 mg of the title compound is obtained as colorless foam.

$^1$H-NMR (CDCl$_3$): δ=0.02 and 0.10 ppm (2×s,21H,SiMe$_3$ and SiMe); 0.56 (s,3H,H-18); 0.79 (t,J=7 Hz,6H,H-30 and H-31); 0.83 (s,18H,Si-t-butyl); 0.85 and 0.95 (2×s; 3H,H-21 and C-20-methyl each); 3.02 and 3.08 (2×d,J=9.5 Hz; 1H,H-22 and H-22' each); 3.26 (t,J=7 Hz,2H,H-24); 3.99 (m,2H, H-1 and H-3); 5.70 and 6.07 (2×d,J=11 Hz; 1H,H-6 and H-7 each)

55. (7E)-(1R, 3R)-24-(3-Hydroxy-3-methylbutyl)-20-methyl-19-nor-23-oxa-9,10-secochola-5,7-diene-1,3-diol 56

125 mg (0.17 mmol) of 54 is reacted with 424 mg (1.36 mmol) of tetrabutylammonium fluoride in 10 ml of tetrahydrofuran analogously to 39., and 56 mg of the title compound is obtained as colorless foam.

$^1$H-NMR (CD$_2$Cl$_2$): δ=0.55 ppm (s,3H,H-18); 0.82 and 0.90 (2×s; 3H,H-21 and C-20-methyl each); 1.10 (s,6H,H-28 and H-29); 3.00 and 3.08 (2×d,J=9.5 Hz; 1H,H-22 and H-22' each); 3.30 (t,J=7 Hz,2H,H-24); 3.91 and 3.98 (2×m; 1H,H-1 and H-3 each); 5.77 and 6.20 (2×d,J=11 Hz; 1H,H-6 and H-7 each)

56. (7E)-(1R,3R)-24-(3-Ethyl-3-hydroxypentyl)-20-methyl-19-nor-23-oxa-9,10-secochola-5,7-diene-1,3-diol 57

106 mg (0.14 mmol) of 55 is reacted with 340 mg (1.09 mmol) of tetrabutylammonium fluoride in 10 ml of tetrahydrofuran analogously to 39., and 57 mg of the title compound is obtained as colorless foam. $^1$H-NMR (CD$_2$Cl$_2$): δ=0.54 ppm (s,3H,H-18); 0.77 (t,J=7 Hz,6H,H-30 and H-31); 0.81 and 0.90 (2×s; 3H,H-21 and C-20-methyl each); 1.38 (q,J=7 Hz,4H,H-28 and H-29); 3.00 and 3.08 (2×d,J= 9.5 Hz; 1H,H-22 and H-22' each); 3.30 (t,J=7 Hz,2H,H-24); 3.91 and 3.98 (2×m; 1H,H-1 and H-3 each); 5.77 and 6.20 (2×d,J=11 Hz; 1H,H-6 and H-7 each)

57. [1S-(1α,3aβ,4α,7aα)]-1-[4-(Acetyloxy)-7a-methyloctahydro-1H-inden-1-yl]ethanone 58

19.2 g (76.1 mmol) of [1R-[1α(S*),3aβ,4α,7aα]]-4-(acetyloxy)-α,7a-dimethyloctahydro-1H-indene-1-acetaldehyde (see 24.) is dissolved in 1000 ml of N,N-dimethylformamide, 7.59 g (66.5 mmol) of 1,4-diazabicyclo[2.2.2]octane, 1.14 g (5.7 mmol) of copper(II) acetate-monohydrate and 909 mg (5.7 mmol) of 2,2'-bipyridyl are added and heated to 70° C. with introduction of oxygen. After 24 hours, it is poured on sodium chloride solution, extracted with ethyl acetate, washed with sodium chloride solution, dried on sodium sulfate, the solvent is removed and the residue is chromatographed on silica gel with hexane/ethyl acetate, and 12.75 g of the title compound is obtained as colorless oil.

$^1$H-NMR (CDCl$_3$): δ=0.83 ppm (s,3H,H-18); 2.03 (s,3H, H-21); 2.12 (s,3H,OAc); 2.50 (t,J=9.5 Hz,1H,H-17); 5.19 (m, 1H,H-8)

58. [1S-(1α,3aβ,4α,7aα)]-7a-Methyl-1-(2-methyl-2-oxiranyl)octahydro-1H-inden-4-ol 59

12.75 g (53.5 mmol) of 58 is dissolved in 400 ml of N,N-dimethylformamide and 15.2 g (86 mmol) of trimethylsulfonium iodide is added. It is cooled to 0° C. and 29.8 g (267 mmol) of potassium-tert-butylate is added in portions. It is stirred for 24 more hours at room temperature, and then sodium chloride solution is added. After extraction with ethyl acetate, washing of the organic phase with sodium chloride solution, drying on sodium sulfate and removal of the solvent, the crude product is purified by chromatography on silica gel with hexane/ethyl acetate as solvent, and 7.91 g of the title compound is obtained as colorless oil.

$^1$H-NMR (CDCl$_3$): δ=1.00 ppm (s,3H,H-18); 1.30 (s,3H, H-21); 2.25 (d,J=5 Hz,1H,H-22); 2.43 (d,J=5 Hz,1H,H-22'); 4.02 (m, 1H,H-8)

59. [1S-(1α,3aβ,4α,7aα)]-4-[[Dimethyl(1,1-dimethylethyl)silyl]oxy]-7a-Methyl-1-(2-methyl-2-oxiranyl)octahydro-1H-indene 60

10.19 g (150 mmol) of imidazole and 11.25 g (75 mmol) of tert-butyldimethylsilyl chloride are added to a solution of 7.91 g (37.6 mmol) of 59 in 200 ml of N,N-dimethylformamide and stirred overnight at room temperature. Then, it is poured on sodium chloride solution, extracted with ethyl acetate, the organic phase is washed with sodium chloride solution, dried on sodium sulfate and the solvent is removed. The residue is dissolved in 50 ml of diethyl ether and instilled at 0° C. in a solution of lithium diethylamide [2.77 g (37.8 mmol) of diethylamine, 24.28 ml of n-butyllithium solution (1.6M in hexane)]. It is stirred again for 24 hours at room temperature, sodium chloride solution is added, extracted with ethyl acetate, the organic phase is washed with sodium chloride solution, dried on sodium sulfate and the solvent is removed. Chromatographic purification yields 8.64 g of the title compound as colorless oil.

$^1$H-NMR (CDCl$_3$): δ=0.01 and 0.10 ppm (2×s; 3H,SiMe each); 0.88 (s,9H,Si-t-butyl); 0.90 (s,3H,H-18); 1.36 (s,3H, H-21); 2.31 (d,J=5 Hz,H-22); 2.50 (d,J=5 Hz,H-22'); 4.00 (m, 1H,H-8)

60. [1S-(1α,3aβ,4α,7aα)]-4-[[Dimethyl(1,1-dimethylethyl) silyl]oxy]-7a-methyl-β-methyleneoctahydro-1H-indene-1-ethanol 61

8.46 g (26.06 mmol) of 60 is dissolved in 500 ml of toluene, mixed with 10.8 g (53.2 mmol) of aluminum isopropylate and stirred overnight at 120° C. After cooling, water/isopropanol is added, it is filtered, the filtrate is concentrated by evaporation and the residue is chromatographed on silica gel with hexane/ethyl acetate, and 7.56 g of the title compound is obtained.

$^1$H-NMR (CDCl$_3$): δ=0.01 and 0.02 ppm (2×s; 3H,SiMe each); 0.80 (s,3H,H-18); 0.89 (s,9H,Si-t-butyl); 2.05 (t,J=9.5 Hz,1H,H-17); 4.00 (dbr,J=15 Hz,1H,H-22); 4.02 (m, 1H,H-8); 4.10 (dd,J=15.5 Hz,1H,H-22'); 4.92 and 5.20 (2×s, 1H,H-21 each)

61. [1S-[1α,3aβ,4α,7aα]]-1,1-Dimethylethyl-2-[4-[[dimethyl-(1,1-dimethylethyl)silyl]oxy]-7a-methyloctahydro-1H-inden-1-yl]-2-propenoxy]acetate 62

2 g (6.16 mmol) of 61 in 18 ml of toluene is reacted with 27.6 ml of sodium hydroxide solution (25%), 129 mg of tetrabutylammonium hydrogen sulfate and 5.96 g (30.55 mmol) of bromoacetic acid-tert-butyl ester analogously to 3., and 2.67 g of the title compound is obtained as colorless oil.

$^1$H-NMR (CDCl$_3$): δ=0.01 ppm (2×s; 3H, SiMe each); 0.80 (s,3H,H-18); 0.90 (s,9H,Si-t-butyl); 1.50 (s,9H, t-butyl ester); 3.93 (s,2H,H-24); 3.98 (s,2H,H-22); 4.02 (m, 1H,H-8); 4.98 and 5.22 (2×s; 1H,H-21 each)

62. [1S-[1α,3aβ,4α,7aα]]-3-[[[2-[4-[[Dimethyl(1,1-dimethylethyl)silyl]oxy]-7a-methyloctahydro-1H-inden-1-yl]-2-propenyl]oxy]methyl]-3-pentanol 63

The Grignard reagent is prepared from 1.34 g (12.32 mmol) of bromoethane and 300 mg (12.3 mmol) of magnesium chips in 30 ml of tetrahydrofuran and reacted with 2.67 g (6.24 mmol) of 62 analogously to 4. 2.58 g of the title compound is obtained as colorless oil, which is further reacted without purification.

63. [1S-[1α,3aβ,4α,7aα]]-1-[2-[4-[[Dimethyl(1,1-dimethylethyl)silyl]oxy]-7a-methyloctahydro-1H-inden-1-yl]-2-propenoxy]-2-methyl-2-propanol 64

The Grignard reagent is prepared from 2.52 g (21.3 mmol) of iodomethane and 517 mg (21.3 mmol) of magnesium chips in 100 ml of diethyl ether and reacted with 3.4 g (7.7 mmol) of 62 analogously to 4. 2.65 g of the title compound is obtained.

$^1$H-NMR (CDCl$_3$): δ=0.01 ppm (2×s; 3H,SiMe each); 0.80 (s,3H,H-18); 0.88 (s,9H,Si-t-butyl); 1.21 (s,6H,H-26 and H-27); 3.19 and 3.25 (2×d,J=9 Hz; 1H,H-24 and H-24' each); 3.89 and 3.96 (2×d,J=13 Hz; 1H,H-22 and H-22' each); 4.01 (m, 1H,H-8); 4.93 and 5.18 (2×s; 1H,H-21 and H-21' each)

64. [1S-[1α,3aβ,4α,7aα]]-1-[2-(2-Ethyl-2-hydroxybutoxy)-1-methylene ethyl]-7a-methyloctahydro-1H-inden-4-ol 65

2.58g (6.07 mmol) of 63 is dissolved in 60 ml of tetrahydrofuran, 12.4 ml of HF/pyridine (70%) is added and stirred for 3 days at room temperature. Then, it is poured on sodium hydrogen sulfate solution, extracted with ethyl acetate, the organic phase is washed with sodium bicarbonate solution and sodium chloride solution and dried on sodium sulfate. Removal of the solvent and chromatographic purification yield 750 mg of the title compound as colorless oil.

$^1$H-NMR (CDCl$_3$): δ=0.78 ppm (s,3H,H-18); 0.81 (t,J=7 Hz,6H,H-28 and H-29); 1.48 (q,J=7 Hz,4H, H-26 and H-27); 3.17 and 3.23 (2×d,J=9 Hz; 1H,H-24 and H-24' each); 3.81 and 3.90 (2×d,J=12.5 Hz; 1H, H-22 and H-22' each); 4.03 (m, 1H,H-8); 4.89 and 5.14 (2×s; 1H,H-21 and H-21' each)

65. [1S-[1α,3aβ,4α,7aα]]-1-[2-(2-Hydroxy-2-methylpropoxy)-1-methylene ethyl]-7a-methyloctahydro-1H-inden-4-ol 66

2 g (5 mmol) of 64 in 38 ml of acetonitrile and 30 ml of tetrahydrofuran is reacted with 30 ml of HF (40%) and stirred for 3 hours at room temperature. Then, sodium bicarbonate solution is carefully added, extracted with ethyl acetate, washed with sodium chloride solution and dried on sodium sulfate. After removal of the solvent and chromatographic purification, 1.25 g of the title compound is obtained as colorless oil.

$^1$H-NMR (CDCl$_3$): δ=0.85 ppm (s,3H,H-18); 1.22 (s,6H, H-26 and H-27); 3.21 and 3.28 (2×d,J=9 Hz; 1H,H-24 and H-24' each); 3.91 and 3.98 (2×d,J=13 Hz; 1H,H-22 and H-22' each); 4.10 (m, 1H,H-8); 4.97 and 5.22 (2×s; 1H,H-21 and H-21' each)

66. [1S-[1α,3aβ,7aα]]-1-[2-(2-Ethyl-2-hydroxybutoxy)-1-methylene ethyl]-7a-methyloctahydro-4H-inden-4-one 67

720 mg (2.40 mmol) of 65 is reacted with 755 mg (3.51 mmol) of pyridinium chlorochromate in 50 ml of methylene chloride analogously to 30., and 522 mg of the title compound is obtained as colorless oil.

$^1$H-NMR (CDCl$_3$): δ=0.52 ppm (s,3H,H-18); 0.80 (t,J=7 Hz,6H,H-28 and H-29); 1.21 (s,1H,OH); 1.48 (q,J=7 Hz,4H, H-26 and H-27); 3.18 and 3.23 (2×d,J=9.5 Hz; 1H,H-24 and H-24' each); 3.84 and 3.95 (2×d,J=13 Hz; 1H,H-22 and H-22' each); 4.96 and 5.16 (2×s; 1H,H-21 and H-21' each)

67. [1S-[1α,3aβ,7aα]]-1-[2-(2-Hydroxy-2-methylpropoxy)-1-methylene ethyl]-7a-methyloctahydro-4H-inden-4-one 68

600 mg (2.12 mmol) of 66 is reacted with 645 mg (3 mmol) of pyridinium chlorochromate in 40 ml of methylene chloride analogously to 30., and 439 mg of the title compound is obtained as colorless oil.

$^1$H-NMR (CDCl$_3$): δ=0.58 ppm (s,3H,H-18); 1.22 (s,6H, H-26 and H-27); 2.57 (dd, J=10.5,7.5 Hz,1H,H-14); 3.22 and 3.28 (2×d,J=9 Hz; 1H,H-24 and H-24' each); 3.95 and 4.04 (2×d,J=13 Hz; 1H,H-22 and H-22' each); 5.02 and 5.23 (2×s; 1H,H-21 and H-21' each)

68. [1S-[1α,3aβ,7aα]]-1-[2-[[2-Ethyl-2-[(trimethylsilyl)oxy]butoxy]-1-methyleneethyl]-7a-methyloctahydro-4H-inden-4-one 69

522 mg (1.75 mmol) of 67 is reacted with 554 mg (5.1 mmol) of trimethylchlorosilane, 459 mg (6.63 mmol) of imidazole and 0.7 ml of pyridine in 50 ml of diethyl ether analogously to 33., and 343 mg of the title compound is obtained as colorless oil.

$^1$H-NMR (CDCl$_3$): δ=0.01 ppm (s,9H,SiMe$_3$); 0.48 (s,3h, H-18); 0.77 (t,J=7 Hz,6H,H-28 and H-29); 3.11 and 3.18 (2×d,J=9.5 Hz; 1H,H-24 and H-24' each); 3.75 and 3.87 (2×d,J=13 Hz; 1H,H-22 and H-22' each); 4.91 and 5.16 (2×s; H,H-21 and H-21' each)

69. [1S-[1α,3aβ,7aα]]-7a-Methyl-1-[2-[[2-methyl-2-[(trimethylsilyl)oxy]propoxy]-1-methylene ethyl]octahydro-4H-inden-4-one 70

420 mg (1.5 mmol) of 68 is reacted with 325 mg (3 mmol) of trimethylchlorosilane, 408 mg (6 mmol) of imidazole and 0.6 ml of pyridine in 50 ml of diethyl ether analogously to 33., and 445 mg of the title compound is obtained as colorless oil.

$^1$H-NMR (CDCl$_3$): δ=0.10 ppm (s,9H,SiMe$_3$); 0.58 (s,3H, H-18); 1.25 (s,6H,H-26 and H-27); 2.57 (dd,J=10.5,7.5 Hz,1H,H-14); 3.18 and 3.22 (2×d,J=9 Hz; 1H,H-24 and H-24' each); 3.92 and 4.00 (2×d,J=13 Hz; 1H,H-22 and H-22' each); 5.01 and 5.24 (2×s; 1H,H-21 and H-21' each)

70. (7E)-(1R, 3R)-1,3-bis[[Dimethyl(1,1-dimethylethyl) silyl]oxy]-26,27-dimethyl-25-(trimethylsilyl)oxy]19-nor-23-oxa-9,10-secocholesta-5,7,20-triene 71

300 mg (0.81 mmol) of 69 is reacted analogously to 36., and 508 mg of the title compound is obtained as colorless foam.

$^1$H-NMR (CDCl$_3$): δ=0.06 and 0.09 ppm (2×s,12H and 9H, SiMe); 0.47 (s,3H,H-18); 0.83 and 0.84 (2×s; 9H,Si-t-butyl each); 0.85 (t,J=7 Hz,6H,H-28 and H-29); 1.52 (q,J=7

Hz,4H,H-26 and H-27); 3.20 and 3.27 (2×d,J=9.5 Hz; 1H,H-24 and H-24' each); 3.84 and 3.91 (2×d,J=13 Hz; 1H,H-22 and H-22' each); 4.09 (m,2H,H-1 and H-3); 4.97 and 5.20 (2×s; 1H,H-21 and H-21' each); 5.83 and 6.18 (2×d,J=11 Hz; 1H,H-6 and H-7 each)

71. (7E)-(1R,3R)-1,3-bis[[Dimethyl(1,1-dimethylethyl)-silyl]oxy]-25-(trimethylsilyl)oxy-19-nor-23-oxa-9,10-secocholesta-5,7,20-triene 72

352 mg (1 mmol) of 70 is reacted analogously to 36., and 50 mg of the title compound is obtained as colorless foam, which was directly further reacted.

72. (7E)-(1R,3R)-26,27-Dimethyl-19-nor-23-oxa-9,10-secocholesta-5,7,20-triene-1,3,25-triol 73

500 mg (0.68 mmol) of 71 is reacted with 1.70 g (5.44 mmol) of tetrabutylammonium fluoride in 45 ml of tetrahydrofuran analogously to 39., and 217 mg of the title compound is obtained as colorless foam.

$^1$H-NMR (CDCl$_3$): δ=0.40 ppm (s,3H,H-18); 0.82 (t,J=7 Hz,6H,H-28 and H-29); 1.48 (q,J=7 Hz,4H,H-26 and H-27); 3.18 and 3.23 (2×d,J=9 Hz; 1H,H-24 and H-24' each); 3.84 and 3.92 (2×d,J=13 Hz; 1H,H-22 and H-22' each); 3.99 and 4.06 (2×m; 1H,H-1 and H-3 each); 4.92 and 5.11 (2×s; 1H,H-21 and H-21' each); 5.81 and 6.24 (2×d,J=11 Hz; 1H,H-6 and H-7 each)

73. (7E)-(1R,3R)-19-Nor-23-oxa-9,10-secocholesta-5,7,20-triene-1,3,25-triol 74

50 mg (0.07 mmol) of 72 is reacted with 121 mg (0.385 mmol) of tetrabutylammonium fluoride in 10 ml of tetrahydrofuran analogously to 39., and 22.5 mg of the title compound is obtained as colorless foam.

$^1$H-NMR (CD$_2$Cl$_2$): δ=0.40 ppm (s,3H,H-18); 1.10 (s,6H, H-26 and H-27); 3.12 and 3.18 (2×d,J=9 Hz; 1H,H-24 and H-24' each); 3.85 and 3.92 (2×d,J=13 Hz; 1H,H-22 and H-22' each); 3.93 and 4.00 (2×m; 1H,H-1 and H-3 each); 4.91 and 5.10 (2×s; 1H,H-21 and H-21' each); 5.70 and 6.20 (2×d, J=11 Hz; 1H,H-6 and H-7 each) 74. [1S-[1α,3aβ,4α,7aα]]-4-[2-[4-[[Dimethyl(1,1-dimethyl-ethyl)silyl]oxy]-7a-methyloctahydro-1H-inden-1-yl]-2-propenoxy]butanoic acid methyl ester 75

2.30 g (7.09 mmol) of 61 is reacted with 6.45 g (28.4 mmol) of 4-bromobutyric acid orthotrimethyl ester, 9.5 ml of sodium hydroxide solution (50%) and 375 mg of tetrabutylammonium hydrogen sulfate analogously to 11., and 2.31 g of the title compound is obtained as colorless oil.

$^1$H-NMR (CDCl$_3$): δ=0.01 ppm (2×s; 3H,SiMe each); 0.80 (s,3H,H-18); 0.89 (s,9H,Si-t-butyl); 2.42 (t,J=6.5 Hz,2H,H-26); 3.40 (t,J=6.5 Hz,2H,H-24); 3.68 (s,3H, COOMe); 3.85 (s,2H,H-22); 4.01 (m, 1H,H-8); 4.92 and 5.18 (2×s; 1H,H-21 and H-21' each)

75. [1S-[1α,3aβ,4α,7aα]]-1-[2-[4-[[Dimethyl(1,1-dimethyl-ethyl)silyl]oxy]-7a -methyloctahydro -1H-inden -1-yl]-2-propenoxy]-4-methyl-4-pentanol 76

The Grignard reagent is prepared from 1.15 g (8.1 mmol) of iodomethane and 196 mg (8.1 mmol) of magnesium chips in 15 ml of diethyl ether and reacted with 1.15 g (2.7 mmol) of 75 analogously to 4., and 934 mg of the title compound is obtained as colorless oil.

$^1$H-NMR (CDCl$_3$): δ=0.01 ppm (2×s; 3H,SiMe each); 0.80 (s,3H,H-18); 0.88 (s,9H,Si-t-butyl); 1.21 (s,6H,H-28 and H-29); 3.42 (m,2H,H-24); 3.88 (s,2H,H-22); 4.01 (m, 1H,H-8); 4.92 and 5.18 (2×s; 1H,H-21 and H-21' each)

76. [1S-[1α,3aβ,4α,7aα]]-1-[2-[4-[[Dimethyl(1,1-dimethyl-ethyl)silyl]oxy]-7a-methyloctahydro-1H-inden-1-yl]-2-propenoxy]-4-ethyl-4-hexanol 77

The Grignard reagent is prepared from 882 mg (8.1 mmol) of bromoethane and 196 mg (8.1 mmol) of magnesium chips in 15 ml of tetrahydrofuran and reacted with 1.15 g (2.7 mmol) of 75 analogously to 4., and 734 mg of the title compound is obtained as colorless oil.

$^1$H-NMR (CDCl$_3$): δ=0.01 ppm (2×s; 3H,SiMe each); 0.80 (s,3H,H-18); 0.88 (t,J=7 Hz,6H,H-30 and H-31); 0.89 (s,9H,Si-t-butyl); 1.48 (q,J=7 Hz,4H,H-28 and H-29); 3.42 (m,2H,H-24); 3.88 (s,2H,H-22); 4.02 (m, 1H,H-8); 4.93 and 5.20 (2×s; 1H,H-21 and H-21' each) 77. [1S-[1α,3aβ,4α,7aα]]-1-[2-(4-Hydroxy-4-methylpentoxy)-1-methylene ethyl]-7a-methyloctahydro-1H-inden-4-ol 78

580 mg (1.37 mmol) of 76 is reacted with 4.41 ml of HF/pyridine (70%) in 30 ml of tetrahydrofuran analogously to 64., and 156 mg of the title compound is obtained as colorless oil.

$^1$H-NMR (CDCl$_3$): δ=0.78 ppm (s,3H,H-18); 1.18 (s,6H, H-28 and H-29); 3.48 (m,2H,H-24); 3.82 (s,2H,H-22); 4.03 (m, 1H,H-8); 4.89 and 5.15 (2×s; 1H,H-21 and H-21' each) 78. [1S-[1α,3aβ,4α,7aα]]-1-[2-[4-Ethyl-4-hydroxyhexoxy) -1-methylene ethyl]-7a-methyloctahydro-1H-inden-4-ol 79

734 mg (1.62 mmol) of 77 is reacted with 5.22 ml of HF/pyridine (70%) in 35 ml of tetrahydrofuran analogously to 64., and 200 mg of the title compound is obtained as colorless oil.

$^1$H-NMR (CDCl$_3$): δ32 0.77 ppm (s,3H,H-18); 0.78 (t,J=7 Hz,6H,H-30 and H-31); 1.40 (q,J=7 Hz,4H,H-28 and H-29); 3.34 (m,2H,H-24); 3.70 (s,2H,H-22); 4.03 (m, 1H,H-8); 4.88 and 5.14 (2×s; 1H,H-21 and H-21' each)

79. [1S-[1α,3aβ,7aαβ]]-1-[2-(4-Hydroxy-4-methylpentoxy) -1-methylene ethyl]-7a -methyloctahydro -1H-inden-4-one 80

150 mg (0.48 mmol) of 78 is reacted with 144 mg (0.67 mmol) of pyridinium chlorochromate in 10 ml of methylene chloride analogously to 29., and 124 mg of the title compound is obtained as colorless oil. $^1$H-NMR (CDCl$_3$): δ=0.58 ppm (s,3H,H-18); 1.23 (s,6H,H-28 and H-29); 2.57 (dd, J=10.5,7.5 Hz,1H, H-14); 3.42 and 3.50 (2×dt,J=9.7 Hz; 1H,H-24 and H-24' each); 3.90 and 3.97 (2×d,J=12.5 Hz; 1. H,H-22 and H-22' each); 5.02 and 5.24 (2×s; 1H,H-21 and H-21' each)

80. [1S-[1α,3aβ,7aα]]-1-[2-(4-Ethyl-4-hydroxyhexoxy)-1-methylene ethyl]-7a-methyloctahydro-4H-inden-4-one 81

200 mg (0.59 mmol) of 79 is reacted with 177 mg (0.83 mmol) of pyridinium chlorochromate in 10 ml of methylene chloride analogously to 30., and 145 mg of the title compound is obtained as colorless oil.

$^1$H-NMR (CDCl$_3$): δ=0.58 ppm (s,3H,H-18); 0.88 (t,J=7 Hz,6H,H-30 and H-31); 1.50 (q,J=7 Hz,4H,H-28 and H-29); 2.58 (dd, J=10.5,7.5 Hz,1H,H-14); 3.40 and 3.48 (2×dt,J= 9.7 Hz; 1H,H-24 and H-24' each); 3.89 and 3.96 (d,J=12.5 Hz; 1H,H-22 and H-22' each); 5.01 and 5.23 (2×s; 1H,H-21 and H-21' each)

81. [1S-[1α,3aβ,7aα]]-1-[2-[4-Methyl-4-[(trimethylsilyl)-oxy]pentoxy]-1-methylene ethyl]-7a-methyloctahydro-4H-inden-4-one 82

120 mg (0.39 mmol) of 80 is reacted with 127 mg (1.17 mmol) of trimethylchlorosilane, 105 mg (1.52 mmol) of imidazole and 0.16 ml of pyridine in 10 ml of diethyl ether analogously to 33., and 119 mg of the title compound is obtained as colorless oil.

$^1$H-NMR (CDCl$_3$): δ32 0.10 ppm (s,9H,SiMe$_3$); 0.58 (s,3H,H-18); 1.12 (s,6H,H-28 and H-29); 2.57 (dd,J=10.5, 7.5 Hz,1H,H-14); 3.38 and 3.43 (2×dt,J=9.7 Hz; 1H, H-24 and H-24' each); 3.88 and 3.96 (2×d,J=12.5 Hz; 1H, H-22 and H-22' each); 5.01 and 5.23 (2×s; 1H,H-21 and H-21' each)

82. [1S-[1α,3aβ,7aα]]-1-[2-[4-Ethyl-4-[(trimethylsilyl)-oxy]hexoxy]-1-methyleneethyl]-7a-methyloctahydro-4H-inden-4-one 83

140 mg (0.42 mmol) of 81 is reacted with 136 mg (1.26 mmol) of trimethylchlorosilane, 113 mg (1.64 mmol) of imidazole and 0.17 ml of pyridine in 10 ml of diethyl ether analogously to 33., and 136 mg of the title compound is obtained as colorless oil.

$^1$H-NMR (CDCl$_3$): δ32 0.01 ppm (s,9H,MeSi); 0.49 (s,3H,H-18); 0.71 (t,J=7 Hz,6H,H-30 and H-31); 1.39 (q,J=7

Hz,4H,H-28 and H-29); 2.47 (dd,J=10.5,7.5 Hz,1H,H-14); 3.26 and 3.33 (2×dt,J=9.7 Hz; 1H,H-24 and H-24' each); 3.79 and 3.87 (2×d,J=12.5 Hz; 1H,H-22 and H-22' each); 4.91 and 5.14 (2×s; 1H,H-21 and H-21' each)

83. (7E)-(1R, 3R)-1,3-bis[[Dimethyl(1,1-dimethylethyl) silyl]oxy]-24-[3-methyl-3-[(trimethylsilyl)oxy]butyl]-19-nor-23-oxa-9,10-secochola-5,7,20-triene 84

110 mg (0.29 mmol) of 82 is reacted analogously to 36., and 125 mg of the title compound is obtained as colorless foam.

¹H-NMR (CDCl₃): δ=0.01 and 0.07 ppm (2×s, 12H and 9H, SiMe); 0.41 (s,3H,H-18); 0.79 and 0.80 (2×s, Si-t-butyl); 1.18 (s,6H,H-28 and H-29); 3.37 (m,2H,H-24); 3.88 (s,2H,H-22); 4.04 (m,2H,H-1 and H-3); 4.93 and 5.15 (2×s; 1H,H-21 and H-21' each); 5.79 and 6.12 (d,J=11 Hz; 1H, H-6 and H-7 each)

84. (7E)-(1R, 3R)-1,3-bis[[Dimethyl(1,1-dimethylethyl)-silyl]oxy]-24-[3-ethyl-3-[(trimethylsilyl)oxy]pentyl]-19-nor-23-oxa-9,10-secochola-5,7,20-triene 85

126 mg (0.31 mmol) of 83 is reacted analogously to 36., and 150 mg of the title compound is obtained as colorless foam.

¹H-NMR (CDCl₃): δ=0.01 and 0.05 ppm (2×s,12H and 9H,SiMe); 0.38 (s,3H,H-18); 0.79 and 0.80 (2×s; 9H,Si-t-butyl each); 0.83 (t,J=7 Hz,6H,H-30 and H-31); 1.38 (q,J=7 Hz,4H,H-28 and M-29); 3.30 (m,2H,H-24); 3.81 (s,2H,H-22); 4.00 (m,2H,H-1 and H-3); 4.89 and 5.10 (2×s; 1H,H-21 and H-21' each); 5.74 and 6.08 (2×d,J=11 Hz; 1H,H-6 and each)

85. (7E)-(1R, 3R)-24-(3-Hydroxy-3-methylbutyl)-19-nor-23-oxa-9,10-secochola-5,7,20-triene-1,3-diol 86

110 mg (0.15 mmol) of 84 is reacted with 374 mg (1.2 mmol) of tetrabutylammonium fluoride in 10 ml of tetrahydrofuran analogously to 39., and 53 mg of the title compound is obtained as colorless foam.

¹H-NMR (CD₂Cl₂): δ=0.38 ppm (s,3H,H-18); 1.12 (s,6H, H-28 and H-29); 3.33 (m,2H,H-24); 3.81 (s,2H, H-22); 3.91 and 3.98 (2×m; 1H,H-1 and H-3 each); 4.90 and 5.10 (2×s; 1H,H-21 and H-21' each); 5.80 and 6.21 (2×d, J=11 Hz; 1H,H-6 and H-7 each)

86. (7E)-(1R,3R)-24-(3-Ethyl-3-hydroxypentyl)-19-nor-23-oxa-9,10-secochola-5,7,20-triene-1,3-diol 87

132 mg (0.17 mmol) of 85 is reacted with 424 mg (1.36 mmol) of tetrabutylammonium fluoride in 10 ml of tetrahydrofuran analogously to 39., and 59 mg of the title compound is obtained as colorless foam.

¹H-NMR (CD₂Cl₂): δ=0.39 ppm (s,3H,H-18); 0.77 (t,J=7 Hz,6H,H-30 and H-31); 1.38 (q,J=7 Hz,4H,H-28 and H-29); 3.32(m,2H,H-24); 3.80 (s,2H,H-22); 3.91 and 3.98 (2×m; 1H,H-1 and H-3 each); 4.89 and 5.09 (2×s; 1H,H-21 and H-21' each); 5.80 and 6.21 (2×d,J=11 Hz; 1H,H-6 and each)

87. (5Z, 7E)-(1S, 3R)-1,3-bis[[1,1-Dimethylethyl) diphenyl-silyl]oxy]-20-formyl-9,10-secopregna-5,7,10 (19),20-tetraene 88

2.8 g (3.36 mmol) of 11 is dissolved in 100 ml of methylene chloride and 11.6 g (133 mmol) of manganese dioxide is added. It is stirred for 1 more hour at room temperature and then suctioned off on Celite. After removal of the solvent, 2.5 g of the title compound is obtained as colorless foam.

¹H-NMR (CDCl₃): δ=0.35 ppm (s,3H,H-18); 0.92 and 0.99 (2×s; 9H,Si-t-butyl each); 4.23 (m, 1H,H-3); 4.55 (m, 1H,H-1); 4.83 and 5.10 (2×s; 1H,H-19 and H-19' each); 6.02 and 6.09 (2×d, J=11 Hz; 1H,H-6 and H-7 each); 6.11 and 6.32 (2×s; 1H,H-21 and H-21' each); 7.23-7.69 (m,20H, Si-phenyl); 9.58 (s,1H,H-22)

88. (5Z,7E,22E)-(1S,3R)-1,3-bis[[(1,1-Dimethylethyl)-diphenylsilyl]oxy]-9,10-secochola-5,7,10(19),20,22-pentaenoic-24-acid methyl ester 89

182 mg (6 mmol) of sodium hydride (80%) is introduced in 10 ml of tetrahydrofuran and 825 mg (4.8 mmol) of dimethyl(methoxycarbonyl)methylphosphonate in 20 ml of tetrahydrofuran is instilled at room temperature. After 30 minutes, 1.2 g (1.5 mmol) of 88 is instilled and stirred overnight. With ice cooling, saturated sodium chloride solution is now instilled, extracted with ethyl acetate, the organic phase is washed with sodium chloride solution, dried on sodium sulfate and the residue is chromatographically purified on silica gel with hexane/ethyl acetate as eluant, and 470 mg of the title compound is obtained as colorless foam.

¹H-NMR (CDCl₃): δ=0.39 ppm (s,3H,H-18); 0.93 and 0.99 (2×s;-9H, Si-t-butyl each); 3.79 (s,3H,COOMe); 4.25 (m, 1H,H-3); 4.57 (m, 1H,H-1); 4.83 and 5.10 (2×s; 1H,H-19 and H-19' each); 5.35 and 5.55 (2×s; 1H,H-21 and H-21' each); 6.05 (d,J=1S.5 Hz,1H, H-23); 6.09 and 6.20 (2×d,J= 11 Hz; 1H,H-6 and H-7 each); 7.24–7.69 (m,20H,Si-phenyl)

89. (5̃7Z,7E, 22E)-(1S, 3R)-1,3-bis[[(1,1-Dimethylethyl)-diphenylsilyl]oxy]-9,10-secochola-5,7,10 (19),20,22-pentaen-24-ol 90

470 mg (0.52 mmol) of 89 is introduced in 60 ml of tetrahydrofuran and 2.16 ml of DIBAH solution (1.3M in toluene) is instilled at 0° C. It is stirred for 1 hour at 0° C., then diluted with toluene, 0.1 ml of isopropanol and 1.05 ml of water are added and stirred for 30 minutes at room temperature. After filtration, the solvent is removed and the residue is chromatographically purified, and 450 mg of the title substance is obtained as colorless foam.

¹H-NMR (CDCl₃): δ=0.40 ppm (s,3H,H-18); 0.94 and 0.99 (2×s; 9H, Si-t-butyl each); 4.20 (m,3H,H-3 and H-24); 4.57 (t,J=5.5 Hz,1H,H-1); 4.83 (s,1H,H-19); 5.00 (s,1H,H-21); 5.10 (s,1H,H-19'); 5.22 (s,1H,H-21'); 6.00 (dt,J=16,5.5 Hz,1H,H-23); 6.01 and 6.09 (2×d,J=11 Hz; 1H,H-6 and H-7 each); 6.27 (d,J=16 Hz,1H,H-22); 7.12–7.70 (m, 20H, Si-phenyl)

90. [(5Z, 7E, 22E)-(1S, 3R)-1,3-bis[[(1,1-Dimethylethyl)-diphenylsilyl]oxy]-9,10-secochola-5,7,10 (19),20,22-pentaene-24-oxy]acetic acid-1,1-dimethylethyl ester 91

450 mg (0.53 mmol) of 90 is reacted with 2.7 ml of sodium hydroxide solution (25%), 11 mg of tetrabutylammonium hydrogen sulfate and 760 mg (3.9 mmol) of bromoacetic acid-tert-butyl ester analogously to 3., and 340 mg of the title compound is obtained as colorless foam.

¹H-NMR (CDCl₃): δ=0.40 ppm (s,3H,H-18); 0.94 and 1.12 (2×s; 9H, Si-t-butyl each); 1.28 (s, 9H, t-butyl ester); 3.98 (s,2H,H-26); 4.15 (d,J=5.5 Hz,2H,H-24); 4.25 (m, 1H,H-3); 4.56 (m, 1H,H-1); 4.84 (s,1H,H-19); 5.01 (s,1H, H-21); 5.10 (s;1H,H-19'); 5.22 (s,1H,H-21'); 5.90 (dt,J= 15.5,5.5 Hz,1H,H-23); 6.28 (d,J=15.5 Hz,1H,H-22); 6.03 and 6.10 (2×d,J=11 Hz; 1H,H-6 and H-7 each); 7.24–7.70 (m, 20H, Si-phenyl)

91. (5Z,7E,22E)-(1S,3R)-24-(2-Hydroxy-2-methylpropoxy)-9,10-secochola-5,7,10 (19),20,22-pentaene-1,3-diol 92

The Grignard reagent is prepared from 397 mg (2.8 mmol) of iodomethane and 69 mg (2.8 mmol) of magnesium chips in 5 ml of diethyl ether and reacted with 340 mg (0.35 mmol) of 91 analogously to 4., and 210 mg of crude product is obtained, which is dissolved in 5 ml of tetrahydrofuran and is reacted with 1 ml of tetrabutylammonium fluoride solution (1M in tetrahydrofuran) analogously to 14. After purification, 60 mg of the title compound is isolated as colorless foam.

¹H-NMR (CD₂Cl₂): δ=0.42 ppm (s,3H,H-18); 1.20 (s,6H, H-28 and H-29); 3.25 (s,2H, H-26); 4.08 (d,J=5.5 Hz,2H, H-24); 4.13 (m, 1H,H-3); 4.38 (m, 1H,H-1); 4.97 (s,1H,H-19); 5.00 and. 5.20 (2×s; 1H,H-21 and H-21' each); 5.30 (s,1H,H-19'); 5.90 (dt,J=15.5,5.5 Hz,1H,H-23); 6.05 and 6.35 (2×d,J=11 Hz; 1H,H-6 and H-7 each); 6.25 (d, J=15.5 Hz, 1H, H-22)

92. (5Z,7E,22E)-(1S,3R)-24-(2-Ethyl-2-hydroxybutoxy)-9, 10-secochola-5,7,10(19),20,22-pentaene-1,3-diol 93

The Grignard reagent is prepared from 136 mg (1.25 mmol) of bromoethane and 30 mg (1.25 mmol) of magnesium chips in 5 ml of tetrahydrofuran and reacted with 120 mg (0.12 mmol) of 92 analogously to 4., and 110 mg of crude product is obtained that is dissolved in 5 ml of tetrahydrofuran and reacted with 1 ml of tetrabutylammonium fluoride solution (1M in tetrahydrofuran) analogously to 14. After purification, 21 mg of the title compound is isolated as colorless foam.

$^1$H-NMR (CD$_2$Cl$_2$): δ=0.37 ppm (s,3H,H-18); 0.78 (t,J=7 Hz,6H,H-30 and H-31); 1.40 (q,J=7 Hz,4H,H-28 and H-29); 3.20(s,2H,H-26); 3.97 (d,J=5.5 Hz,2H,H-24); 4.10 (m, 1H,H-3); 4.31 (m, 1H,H-1); 4.89 (s,1H,H-19); 4.91 and 5.12 (2×s; 1H,H-21 and H-21' each); 5.23 (s,1H,H-19'); 5.81 (dt,J=15.5,5.5 Hz,1H,H-24); 5.98 and 6.30 (2×d,J=11 Hz; 1H,H-6 and H-7 each); 6.18 (d,J=15.5 Hz,1H,H-22)

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A vitamin D compound of the formula

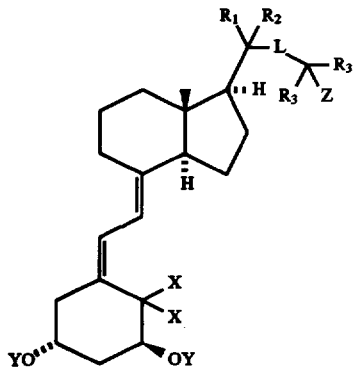

in which

Y means a hydrogen atom, an alkanoyl group of 1 to 9 carbon atoms, or an aroyl group, wherein each Y is chosen independently;

Z means a hydrogen atom, a hydroxyl group or an alkanoyloxy group of 1 to 9 carbon atoms, X means a hydrogen atom or both X's together mean an exocyclic methylene group, R$_1$ and R$_2$, independent of one another, mean an alkyl group of 1 to 4 carbon atoms, R$_3$ means a linear or branched alkyl group of 1 to 5 carbon atoms or a trifluoromethyl group, or the two R$_3$ groups together with carbon atom 25 form a cyclopropyl or cyclopentyl ring, L means the grouping

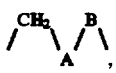

in which

A represents an oxygen atom, and B represents an alkylene group —(CH$_2$)$_n$—, in which n=1, 2, 3, 4, 5 or 6, or L means grouping

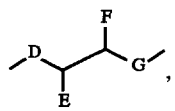

in which

D represents a direct bond, a methylene bridge or a 1,2-ethenediyl bridge (E-double bond) between carbon atoms 20 and 22, E and F respectively represent a hydrogen atom, or together a second bond (E-double bond), and G represents a direct bond or an alkylene group —(CH$_2$)$_n$—, in which n=1, 2, 3, 4, 5 or 6 or a corresponding alkylene group in which a methylene group is replaced by an oxygen atom with the proviso that when the two X's together mean a methylene group, at least one of R$_1$ and R$_2$ is not a methyl group.

2. A vitamin D compound according to claim 1, wherein Y are hydrogen atoms or alkanoyl radicals of saturated alkanecarboxylic acids or of the benzoyl radical and Z is a hydroxyl group or an alkanoyloxy radical of saturated alkanecarboxylic acids or of the benzoyloxy radical.

3. A vitamin D compound according to claim 1, wherein the methyl, ethyl or propyl group or a cyclopropyl or cyclopentyl ring formed together with the tertiary carbon atom 25 stands for R$_3$.

4. A vitamin D compound according to claim 1, wherein both Y's each stand for a hydrogen atom, Z stands for a hydroxyl group and R$^3$ each stand for a methyl, ethyl or propyl group.

5. A pharmaceutical preparation comprising a compound according to claim 1, and a pharmaceutically compatible vehicle.

6. The pharmaceutical preparation according to claim 5, wherein the vehicle is suitable for topical use.

7. A compound according to claim 1, wherein R$_1$ and R$_2$ are each an alkyl and both X each a hydrogen.

8. A vitamin D compound according to claim 1, wherein L is the grouping —CH$_2$—A—B—.

9. A vitamin D compound according to claim 1, wherein each X is a hydrogen atom and the 17 position side chain is one of the following:

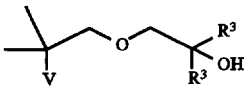

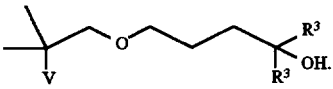

10. A vitamin D compound according to claim 9, wherein Z is a hydroxy group.